United States Patent
Becker et al.

(10) Patent No.: US 9,758,671 B2
(45) Date of Patent: Sep. 12, 2017

(54) STRAIN-PROMOTED CROSSLINKING OF PEG-BASED HYDROGELS VIA COPPER-FREE CYCLOADDITION

(71) Applicants: Matthew Becker, Stow, OH (US); Robert A. Weiss, Akron, OH (US)

(72) Inventors: Matthew Becker, Stow, OH (US); Robert A. Weiss, Akron, OH (US)

( * ) Notice: Subject to any disclaimer, the term of this patent is extended or adjusted under 35 U.S.C. 154(b) by 98 days.

(21) Appl. No.: 14/418,507

(22) PCT Filed: Jul. 31, 2013

(86) PCT No.: PCT/US2013/052911
§ 371 (c)(1),
(2) Date: Jan. 30, 2015

(87) PCT Pub. No.: WO2014/022501
PCT Pub. Date: Feb. 6, 2014

(65) Prior Publication Data
US 2015/0183988 A1    Jul. 2, 2015

Related U.S. Application Data

(60) Provisional application No. 61/677,683, filed on Jul. 31, 2012.

(51) Int. Cl.
| | | |
|---|---|---|
| C12N 5/00 | (2006.01) | |
| C08L 71/00 | (2006.01) | |
| C08G 65/325 | (2006.01) | |
| C08G 65/333 | (2006.01) | |
| C08L 71/02 | (2006.01) | |
| C08L 89/00 | (2006.01) | |
| A61K 9/06 | (2006.01) | |
| A61K 47/34 | (2017.01) | |

(52) U.S. Cl.
CPC ............ *C08L 71/00* (2013.01); *A61K 9/06* (2013.01); *A61K 47/34* (2013.01); *C08G 65/325* (2013.01); *C08G 65/33389* (2013.01); *C08L 71/02* (2013.01); *C08L 89/00* (2013.01); *C08L 2205/02* (2013.01)

(58) Field of Classification Search
None
See application file for complete search history.

(56) References Cited

U.S. PATENT DOCUMENTS

| | | | | |
|---|---|---|---|---|
| 2009/0220607 A1* | 9/2009 | Kiser | .................. | A61K 31/787 514/1.1 |
| 2010/0121022 A1* | 5/2010 | Musa | ................. | C08G 73/0605 528/319 |
| 2012/0100103 A1* | 4/2012 | Park | ....................... | A61L 27/52 424/85.2 |

FOREIGN PATENT DOCUMENTS

WO    WO 2012/126005 A2 *  9/2012

OTHER PUBLICATIONS

Zheng et al. ACS Macro. Lett. (Aug. 21, 2012; web publication Aug. 7, 2012) 8(1): 1071-1073.*
Nguyen et al. Macromol. Chem. Phys. (Apr. 25, 2013) 214: 948-956 with supporing inforamtion pp. 1-10.*
Xu et al. Chem. Asian J. (Oct. 4, 2011) 6: 2730-2737.*

* cited by examiner

*Primary Examiner* — Susan Hanley
(74) *Attorney, Agent, or Firm* — Renner Kenner Greive Bobak Taylor Weber

(57) ABSTRACT

The present invention is directed to a covalently crosslinked hydrogel comprising the strain-promoted reaction product of an 8-member cycloalkyne functionalized polyalkylene glycol and a multi-arm glycerol exytholate triazide and methods for making them. Because the precursor materials can be manipulated without causing crosslinking, provided the strain threshold is not reached, these hydrogels permit mechanical control over when (and where) cross linking occurs and are easier to use than prior strain-activated or temperature-activated systems. These novel hydrogels do not require a catalyst to cross link, thus avoiding the biocompatibility problems common to many catalysts. Nor is the crosslinking process affected by the presence of catalysts or other substances, which have interfered with crosslinking in known strain induced hydrogels. Because of their crosslinking reaction kinetics, these novel hydrogels can encapsulate and transport highly sensitive cells and other biological additives and have no known toxic byproducts.

30 Claims, 15 Drawing Sheets

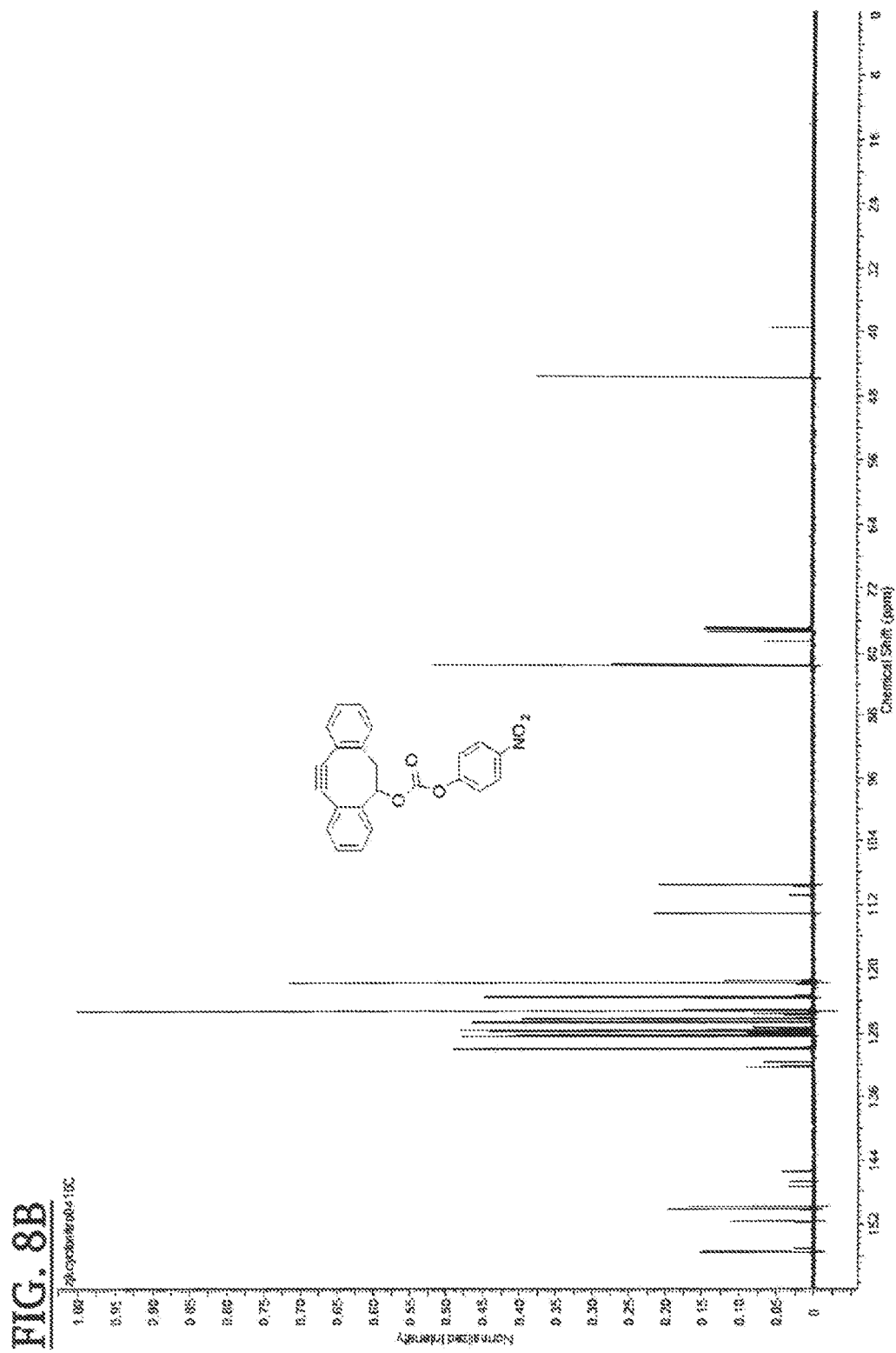

STRAIN-PROMOTED CROSSLINKING OF PEG-BASED HYDROGELS VIA COPPER-FREE CYCLOADDITION

CROSS REFERENCE TO RELATED APPLICATIONS

This application claims the benefit of U.S. provisional patent application Ser. No. 61/677,683 entitled "Strain-Promoted Crosslinking of PEG-based Hydrogels via Copper-Free Cycloaddition," filed Jul. 3, 2012, and incorporated by reference in its entirety.

REFERENCE TO GOVERNMENT SUPPORT

The invention was developed at least in part with the support of the National Institute of Health grant number MLB, P41 EB0063536. The government may have certain rights in the invention.

FIELD OF THE INVENTION

The present invention is in the field of strain-promoted, covalently crosslinked hydrogels and relates to covalently crosslinked hydrogel comprising the strain-promoted reaction product of an 8-member cycloalkyne functionalized polyalkylene glycol and a multi-arm glycerol ethoxylate triazide, and processes for their making.

BACKGROUND OF THE INVENTION

Polymeric hydrogels are well known in the art and can be defined as two- or multicomponent systems consisting of a three-dimensional network of polymer chains and water that fills the space between macromolecules. A hydrogel is a network of polymer chains that are water-insoluble, sometimes found as a colloidal gel in which water is the dispersion medium. Hydrogels are superabsorbent (they can contain over 99% water) natural or synthetic polymers. Hydrogels possess also a degree of flexibility very similar to natural tissue, due to their significant water content.

Hydrogels are commonly used in soft contact lenses, wound dressings, drug-delivery systems, superabsorbents, a number of medical and regenerative medicine applications. Depending on the properties of the polymer (polymers) used, as well as on the nature and density of the network joints, such structures in an equilibrium can contain various amounts of water; typically in the swollen state the mass fraction of water in a hydrogel is much higher than the mass fraction of polymer.

Two general classes of hydrogels have been defined. The first are physical hydrogels, where the chains are connected by electrostatic forces, hydrogen bonds, hydrophobic interactions or chain entanglements (such gels are non-permanent and usually they can be converted to polymer solutions by heating). Physical cross-linking of polymer chains can be achieved using a variety of environmental triggers (pH, temperature, ionic strength) and a variety of physicochemical interactions (hydrophobic interactions, charge condensation, hydrogen bonding, or supramolecular interactions). The presence of reversible crosslinking points in physically crosslinked hydrogels allows solvent casting and/or thermal processing. The major disadvantage of physically crosslinked hydrogels, however, is their weak mechanical properties in the swollen state and the range of materials that can be triggered to form in physiologically relevant conditions are extremely limited.

The second class of hydrogels is chemical hydrogels, which generally have covalent bonds linking the chains. Chemical methods include various click reactions, thiolene additions, metal-catalyzed azide-alkyne cycloadditions, Michael additions and Diels-Alder reactions. Metal-free, strain-promoted azide-alkyne "click" cycloaddition reactions have been applied to cell imaging as well as hydrogels systems due to its highly efficient conversion, orthogonality, and bio-friendly characteristics. The gel formation process is atom neutral in that there are not residuals that contaminate the system and could pose toxicity problems to associated biological systems The onset of gel formation in these systems has typically been dependent on chemical or photochemical processes to initiate network formation from monomeric precursors. The use of bioincompatible initiating systems (such as chemical catalysts, heat, and/or ultraviolet (UV) light), and the presence of residual metal catalysts, organic solvents, and the incomplete conversion of the functional groups often lead to biocompatibility problems with these systems. The experimental demands for each of these gelation and functionalization strategies places distinct constraints on the utility and versatility of the respective hydrogels and make direct clinical translation difficult or impossible.

More recently, injectable hydrogels that form in situ have been found to hold additional promise, as they are adaptable to complicated defect sites relative to preformed hydrogels. In these systems, one or more solutions containing the constituent monomers of the hydrogel are injected or otherwise delivered to the site where the hydrogel is to be used and crosslinking is initiated. A common problem with these systems is that the photochemical, heat, UV light, and or chemical catalyst based initiators required for crosslinking of the polymer network are often not very biocompatible and do not work with sensitive cell types. Moreover, all of the byproducts of the crosslinking reaction must also be biocompatible and the presence of residual metal catalysts, organic solvents, and the incomplete conversion of the functional groups often lead to biocompatibility problems with these systems In-situ forming hydrogels that are initiated by physical strain have also been developed. Many of these systems, however, will not crosslink in the presence of gelatins, collagens, lipids, carbohydrates or polymer nanofibers, significantly limiting their usefulness.

Accordingly, what is needed in the art is a hydrogel that is capable of being formed in situ (and in vivo), has no toxic byproducts, permits mechanical control of when (and where) cross linking occurs, is easier to use than heat based systems, and will cross link in the presence of gelatins, collagens, lipids, carbohydrates or polymer nanofibers.

SUMMARY OF THE INVENTION

The present invention is directed to a covalently crosslinked hydrogel comprising the strain-promoted reaction product of an 8-member cycloalkyne functionalized polyalkylene glycol and a multi-arm glycerol ethoxylate triazide. The covalently crosslinked hydrogels of the present invention permit mechanical control over when (and where) cross linking will occur and are easier to use than prior strain-activated or temperature-activated systems.

The precursor materials can be manipulated, without causing crosslinking, so long as the strain threshold is not reached. The hydrogel does not require a catalyst to cross link, thus avoiding the biocompatibility problems common to many catalysts. Nor is the crosslinking process affected by the presence of catalysts or other substances that can interfere with crosslinking in known strain induced hydrogels. The precursor materials are substantially orthogonal and will crosslink in the presence of gelatins, collagens, lipids, carbohydrates or polymer nanofibers. Because of their crosslinking reaction kinetics, the hydrogels of the present invention can encapsulate and transport highly sensitive cells and other biological additives. Moreover, the hydrogels of the present invention have no known toxic byproducts.

Moreover, the covalently crosslinked hydrogels are versatile and biocompatible since they are based on a metal free, strain-promoted azide-alkyne cycloaddition process. No light, no initiator and no catalyst are required for crosslinking. Nothing that is harmful to sensitive proteins, peptides or cells is required.

The present invention further includes effective methods for the encapsulation of cells and other sensitive biological materials within hydrogels where gelation is based on the cumulative effects of specific molecular-recognition interactions between strained cyclocotyne units and azide terminated PEG chains. The potential variability in the molecular mass of the respective components, number of branch units and compatibility with both hMSCs and cell media provides versatility in applications where syringe injectable materials or in situ formation of hydrogels are necessary.

In some embodiments, the present invention is directed to a covalently crosslinked hydrogel comprising the strain-promoted reaction product of an 8-member cycloalkyne functionalized polyalkylene glycol and a multi-arm glycerol ethoxylate triazide. In some embodiments, the covalently crosslinked hydrogel of the present invention may include the embodiments described above wherein the 8-member cycloalkyne functionalized polyalkylene glycol is a polymer selected from the group consisting of polyethylene glycol, polypropylene glycol and combinations thereof. In some embodiments, the covalently crosslinked hydrogel of the present invention may include any of the embodiments described above wherein said 8-member cycloalkyne functionalized polyalkylene glycol has a molecular mass from about 500 Da to about 12000 Da.

In some embodiments, the covalently crosslinked hydrogel of the present invention may include any of the embodiments described above wherein said 8-member cycloalkyne functionalized polyalkylene glycol is dibenzylcyclooctyne functionalized polyethylene glycol.

In some embodiments, the covalently crosslinked hydrogel of the present invention may include any of the embodiments described above wherein said 8-member cycloalkyne functionalized polyalkylene glycol is an aqueous solution comprising from about 1% to about 40% weight percent dibenzylcyclooctyne functionalized polyethylene glycol. In some embodiments, the covalently crosslinked hydrogel of the present invention may include any of the embodiments described above wherein said 8-member cycloalkyne functionalized polyalkylene glycol is an aqueous solution comprising about 11 weight percent dibenzylcyclooctyne functionalized polyethylene glycol.

In some embodiments, the covalently crosslinked hydrogel of the present invention may include any of the embodiments described above wherein said multi-arm glycerol ethoxylate triazide is a glycerol ethoxylate triazide having from 2 to 5 arms. In some embodiments, the covalently crosslinked hydrogel of the present invention may include any of the embodiments described above wherein said multi-arm glycerol ethoxylate triazide is a 3-arm glycerol ethoxylate triazide.

In some embodiments, the covalently crosslinked hydrogel of the present invention may include any of the embodiments described above wherein said multi-arm glycerol ethoxylate triazide is an aqueous solution comprising from about 1% to about 40% weight percent of a 3-arm glycerol ethoxylate triazide. In some embodiments, the covalently crosslinked hydrogel of the present invention may include any of the embodiments described above wherein said multi-arm glycerol ethoxylate triazide is an aqueous solution comprising about 3% weight percent of a 3-arm glycerol ethoxylate triazide.

In some embodiments, the covalently crosslinked hydrogel of the present invention may include any of the embodiments described above wherein said covalently crosslinked hydrogel is formed by the strain-promoted cycloaddition of said dibenzylcyclooctyne functionalized polyethylene glycol and said multi-arm glycerol ethoxylate triazide. In some embodiments, the covalently crosslinked hydrogel of the present invention may include any of the embodiments described above wherein said covalently crosslinked hydrogel is formed by the strain-promoted cycloaddition of said 8-member cycloalkyne functionalized polyalkylene glycol and said 3-arm glycerol ethoxylate triazide. In some embodiments, the covalently crosslinked hydrogel of the present invention may include any of the embodiments described above wherein said covalently crosslinked hydrogel is formed by the strain-promoted cycloaddition of a dibenzylcyclooctyne functionalized polyethylene glycol and a 3-arm glycerol ethoxylate triazide. In some embodiments, the covalently crosslinked hydrogel of the present invention may include any of the embodiments described above wherein said is dibenzylcyclooctyne functionalized polyethylene glycol has a mass average molecular weight of from about 1,000 to about 20,000.

In some embodiments, the covalently crosslinked hydrogel of the present invention may include any of the embodiments described above wherein the covalently crosslinked hydrogel has a crosslink density of from about 2 to about 300 mol/m3. In some embodiments, the covalently crosslinked hydrogel of the present invention may include any of the embodiments described above wherein the covalently crosslinked hydrogel has a crosslink density of about 8.6 mol/m3.

In some embodiments, the covalently crosslinked hydrogel of the present invention may include any of the embodiments described above wherein the covalently crosslinked hydrogel has a loss factor (tan δ) of from about 0.10 to about 0.50. In some embodiments, the covalently crosslinked hydrogel of the present invention may include any of the embodiments described above wherein the covalently crosslinked hydrogel has a loss factor (tan δ) of about 0.25.

In some embodiments, the covalently crosslinked hydrogel of the present invention may include any of the embodiments described above further comprising an additive selected from the group consisting of cells, collagen, decellularized tissue, gelatin and combinations thereof. In some embodiments, the covalently crosslinked hydrogel of the present invention may include any of the embodiments described above wherein said additive is encapsulated with said covalently crosslinked hydrogel. In some embodiments, the covalently crosslinked hydrogel of the present invention may include any of the embodiments described above wherein said additive is human mesenchymal stem cells.

In some embodiments, the covalently crosslinked hydrogel of the present invention may include any of the embodiments described above wherein said covalently crosslinked hydrogel is from about 40% to about 99.9% water. In some embodiments, the covalently crosslinked hydrogel of the present invention may include any of the embodiments described above wherein said covalently crosslinked hydrogel is about 96.1% water.

In some embodiments, the covalently crosslinked hydrogel of the present invention may include any of the embodiments described above wherein said dibenzylcyclooctyne functionalized polyethylene glycol has the following formula:

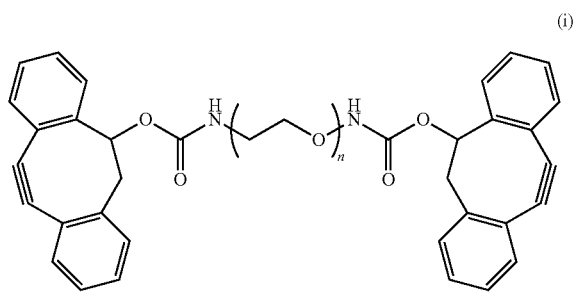

wherein n is an integer from about 60 to about 300. In some embodiments, n is 6 or 7.

In some embodiments, the covalently crosslinked hydrogel of the present invention may include any of the embodiments described above wherein said 3-arm glycerol ethoxylate triazide has the following formula:

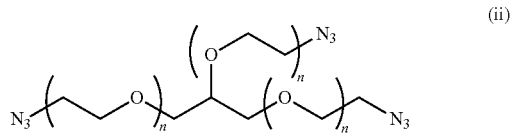

wherein n is an integer from about 8 to about 30.

In some embodiments, the covalently crosslinked hydrogel of the present invention may include any of the embodiments described above having the formula:

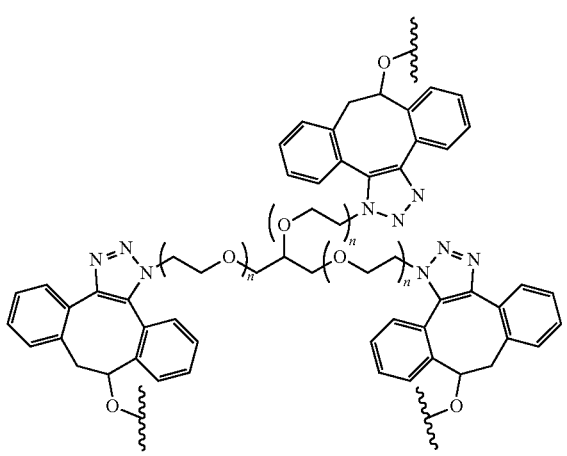

wherein n is an integer from about 8 to about 30.

In other aspects, the present invention is directed to a method of making a covalently crosslinked hydrogel, comprising: (a) preparing an aqueous solution containing a 8-member cycloalkyne functionalized polyalkylene glycol; (b) preparing an aqueous solution containing a multi-arm glycerol ethoxylate triazide; and (c) combining the solution of step (a) with the solution of step (b); and (d) applying a strain to the mixture of step (c) until covalent crosslinks form between said 8-member cycloalkyne functionalized polyalkylene glycol and said multi-arm glycerol ethoxylate triazide.

In some embodiments, the method of making a covalently crosslinked hydrogel of the present invention may include any of the embodiments described above wherein said 8-member cycloalkyne functionalized polyalkylene glycol is a polymer selected from consisting of polyethylene glycol, polypropylene glycol and combinations thereof. In some embodiments, the method of making a covalently crosslinked hydrogel of the present invention may include any of the embodiments described above wherein said 8-member cycloalkyne functionalized polyalkylene glycol is polyethylene glycol. In some embodiments, the method of making a covalently crosslinked hydrogel of the present invention may include any of the embodiments described above wherein said 8-member cycloalkyne functionalized polyalkylene glycol is dibenzylcyclooctyne functionalized polyethylene glycol.

In some embodiments, the method of making a covalently crosslinked hydrogel of the present invention may include any of the embodiments described above wherein the aqueous solution of step (a) contains from about 1% to about 40% weight percent of said 8-member cycloalkyne functionalized polyalkylene glycol. In some embodiments, the method of making a covalently crosslinked hydrogel of the present invention may include any of the embodiments described above wherein the aqueous solution of step (a) contains about 11 weight percent of said 8-member cycloalkyne functionalized polyalkylene glycol.

In some embodiments, the method of making a covalently crosslinked hydrogel of the present invention may include any of the embodiments described above wherein said multi-arm glycerol ethoxylate triazide is a glycerol ethoxylate triazide having from 2 to 5 arms. In some embodiments, the method of making a covalently crosslinked hydrogel of the present invention may include any of the embodiments described above wherein said multi-arm glycerol ethoxylate triazide is a 3-arm glycerol ethoxylate triazide.

In some embodiments, the method of making a covalently crosslinked hydrogel of the present invention may include any of the embodiments described above wherein the aqueous solution of step (b) contains from about 1% to about 40% weight percent of said multi-arm glycerol ethoxylate triazide. The method of claim 29, wherein the aqueous solution of step (b) contains about 3% weight percent of said multi-arm glycerol ethoxylate triazide.

In some embodiments, the method of making a covalently crosslinked hydrogel of the present invention may include any of the embodiments described above wherein said is dibenzylcyclooctyne functionalized polyethylene glycol has a mass average molecular weight of from about 1,000 to about 20,000.

In some embodiments, the method of making a covalently crosslinked hydrogel of the present invention may include any of the embodiments described above further comprising the step of introducing the mixture of step C into a living organism, prior to step (d). In some embodiments, the method of making a covalently crosslinked hydrogel of the present invention may include any of the embodiments described above wherein the mixture of step (d) is introduced into a living organism by injection. In some embodiments, the method of making a covalently crosslinked hydrogel of the present invention may include any of the embodiments described above wherein step D occurs in vivo.

In some embodiments, the method of making a covalently crosslinked hydrogel of the present invention may include any of the embodiments described above wherein the mixture of step (c) is a viscous liquid. In some embodiments, the method of making a covalently crosslinked hydrogel of the present invention may include any of the embodiments described above wherein the mixture of step (c) has a loss factor (tan δ) greater than or equal to about 1.0. In some embodiments, the method of making a covalently crosslinked hydrogel of the present invention may include any of the embodiments described above wherein the mixture of step (c) has a loss factor (tan δ) of about 1.0.

In some embodiments, the method of making a covalently crosslinked hydrogel of the present invention may include any of the embodiments described above further comprising the step of adding an additive selected from the group consisting of cells, collagen, decellularized tissue, gelatin and combinations thereof into one or more of the aqueous solution of step (a), the aqueous solution of step (b), or the mixture of step (c). In some embodiments, the method of making a covalently crosslinked hydrogel of the present invention may include any of the embodiments described above wherein said additive is encapsulated with said covalently crosslinked hydrogel. In some embodiments, the method of making a covalently crosslinked hydrogel of the present invention may include any of the embodiments described above wherein said additive is human mesenchymal stem cells.

In some embodiments, the method of making a covalently crosslinked hydrogel of the present invention may include any of the embodiments described above wherein the strain applied in step (d) is an oscillatory shear strain of from about 5% to about 15%.

BRIEF DESCRIPTION OF THE DRAWINGS

For a more complete understanding of the features and advantages of the present invention, reference is now made to the detailed description of the invention along with the accompanying figures in which:

FIGS. 8A and 8B are $^1$HNMR and $^{13}$CNMR spectra of carbonic acid, 5,6-(dihydro-11,12-didehydro-dibenzo[a,e]cycloocten-5-yl ester, 4-nitrophenyl ester (x).

DETAILED DESCRIPTION OF THE ILLUSTRATIVE EMBODIMENTS

Figure 1:
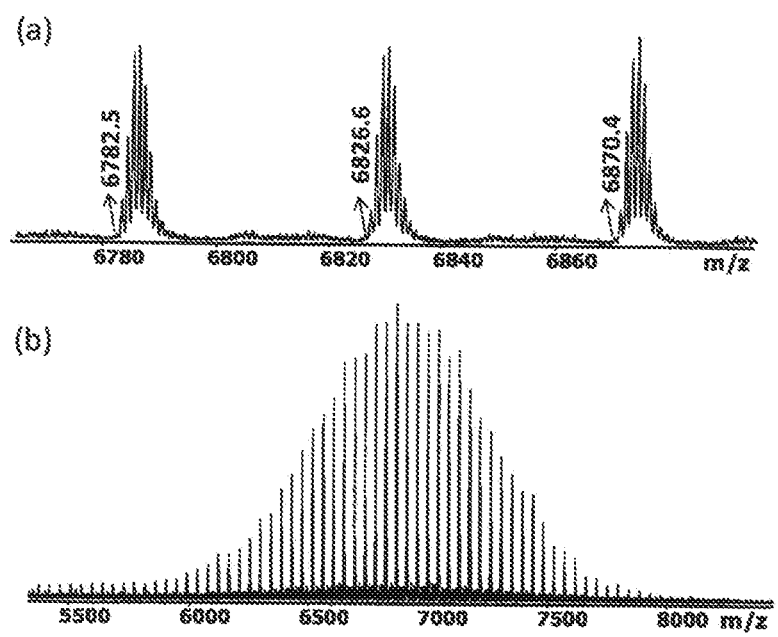
FIG. 1 is mass spectrum of DIBO-PEG (cationized with NaTFA) taken using a matrix-assisted laser desorption/ionization time-of-flight mass spectrometer (MALDI-TOF) made according to at least one embodiment of the present invention. Monoisotopic mass-to-charge ratios (m/z) are marked in the upper spectrum. The measured m/z values agree with the anticipated structure.

In general outline, the present invention is directed to a covalently crosslinked hydrogel formed via a strain-promoted cycloaddition azide-alkyne "click" reactions between 8-member cycloalkyne functionalized polyalkylene glycols and multi-arm glycerol ethoxylate triazides and methods for making them. These metal free, strain-promoted azide-alkyne "click" cycloaddition reactions have been applied to cell imaging as well as hydrogels systems due to their highly efficient conversion, orthogonality, and bio-friendly characteristics. The present invention further includes effective methods for the encapsulation of cells and other sensitive biological materials within the hydrogels where gelation is based on the cumulative effects of specific molecular-recognition interactions between strained cyclocotyne units and azide terminated PEG chains. The potential variability in the molecular mass of the respective components, number of branch units and compatibility with both hMSCs and cell media provides versatility for both in syringe injectable (in vivo) and in situ hydrogel applications.

The 8-member cycloalkyne functionalized polyalkylene glycol component of the hydrogel comprises the two or more alkyne end groups required for the azide-alkyne "click" cycloaddition reaction to take place connected to a polyalkylene glycol backbone. The polyalkylene glycol backbone may be polyethylene glycol (PEG) or polypropylene glycol, or a combination thereof. In some embodiments, the polyalkylene glycol may be PEG.

As set forth above, the polyalkylene glycol component has one or more 8-member cycloalkyne end groups which react with azide end groups on the multi-arm glycerol ethoxylate triazides component to form the covalently crosslinked hydrogel. Any 8-member cycloalkyne capable of being functionalized to a polyalkylene glycol may be used, provided that its auxiliary groups do not interfere with the azide-alkyne "click" cycloaddition reaction or bond with any other substance that does. Suitable 8-member cycloalkyne end groups may include, without limitation, 4-dibenzocyclooctynol (DIBO). In some embodiments, 8-member cycloalkyne may be 4-dibenzocyclooctynol (DIBO).

The 8-member cycloalkyne functionalized polyalkylene glycol may have a molecular mass from about 500 Da to about 12000 Da. In some embodiments, the 8-member cycloalkyne functionalized polyalkylene glycol may have a molecular mass from about 500 Da to about 2,000 Da. In some embodiments, the 8-member cycloalkyne functionalized polyalkylene glycol may have a molecular mass from about 2,001 Da to about 4,000 Da. In some embodiments, the 8-member cycloalkyne functionalized polyalkylene glycol may have a molecular mass from about 4,001 Da to about 8,000 Da. In some embodiments, the 8-member cycloalkyne functionalized polyalkylene glycol may have a molecular mass from about 8,001 Da to about 10,000 Da. In some embodiments, the 8-member cycloalkyne functionalized polyalkylene glycol may have a molecular mass from about 10,001 Da to about 12,000 Da.

The 8-member cycloalkyne functionalized polyalkylene glycol may have from about 6 to about 300 alkylene glycol units. In some embodiments, the 8-member cycloalkyne functionalized polyalkylene glycol may have from about 6 to about 10 alkylene glycol units. In some embodiments, the 8-member cycloalkyne functionalized polyalkylene glycol may have from about 11 to about 50 alkylene glycol units. In some embodiments, the 8-member cycloalkyne functionalized polyalkylene glycol may have from about 51 to about 100 alkylene glycol units. In some embodiments, the 8-member cycloalkyne functionalized polyalkylene glycol may have from about 101 to about 150 alkylene glycol units. In some embodiments, the 8-member cycloalkyne functionalized polyalkylene glycol may have from about 151 to about 200 alkylene glycol units. In some embodiments, the 8-member cycloalkyne functionalized polyalkylene glycol may have from about 201 to about 250 alkylene glycol units. In some embodiments, the 8-member cycloalkyne functionalized polyalkylene glycol may have from about 251 to about 300 alkylene glycol units.

As would be apparent to those of skill in the art, the 8-member cycloalkyne functionalized polyalkylene glycol component will be present in an aqueous solution. The concentration of the 8-member cycloalkyne functionalized polyalkylene glycol component of the hydrogel in the aqueous solution may be from about 1% to about 40%. In some embodiments, the concentration of the 8-member cycloalkyne functionalized polyalkylene glycol component of the hydrogel in the aqueous solution may be from about 10% to about 15%. In some embodiments, the 8-member cycloalkyne functionalized polyalkylene glycol is an aqueous solution comprising from about 1% to about 40% weight percent dibenzylcyclooctyne functionalized polyethylene glycol. In some embodiments, the 8-member cycloalkyne functionalized polyalkylene glycol is an aqueous solution comprising from about 10% to about 15% weight percent dibenzylcyclooctyne functionalized polyethylene glycol. In some embodiments, the 8-member cycloalkyne functionalized polyalkylene glycol is an aqueous solution comprising about 11 weight percent dibenzylcyclooctyne functionalized polyethylene glycol.

In some embodiments, the aqueous solution containing the 8-member cycloalkyne functionalized polyalkylene glycol component of the hydrogel further comprises an additive, which may be incorporated into and encapsulated by the hydrogel. Suitable additives include, but are not limited to, cells, collagen, decellularized tissue, gelatin, proteins, cell media, serum albumin, viruses, pharmaceutical compounds, enzymes, DNA, RNA, Interfering RNA, other small biological agents, and combinations thereof. In some embodiments, the additive is encapsulated within said covalently crosslinked hydrogel.

In some embodiments, is a 4-dibenzocyclooctynol (DIBO) functionalized poly(ethylene glycol) (PEG) polymer. In some embodiments, the 8-member cycloalkyne functionalized polyalkylene glycol component of the hydrogel may be a Dibenzylcyclooctyne Polyethylene glycol. In some embodiments, the 8-member cycloalkyne functionalized polyalkylene glycol has the structure of formula (i).

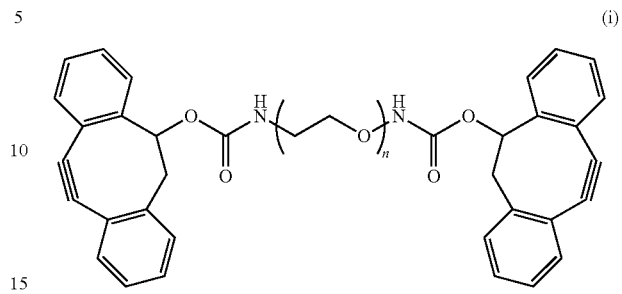

wherein n is an integer from about 6 to about 300. In some embodiments, n is 6 or 7. In some embodiments, n is an integer from about 6 to about 10. In some embodiments, n is an integer from about 11 to about 100. In some embodiments, n is an integer from about 101 to about 200. In some embodiments, n is an integer from about 201 to about 300.

The multi-arm glycerol ethoxylate triazide component of the hydrogel has multiple azide end groups which react with the 8-member cycloalkyne end groups on the component of the 8-member cycloalkyne functionalized polyalkylene glycol component discussed above to form the covalently crosslinked hydrogel. The multi-arm glycerol ethoxylate triazide component of the hydrogel may have from about 2 to about 5 azide end groups, an more preferably about 2 or 3 azide end groups. In some embodiments, the multi-arm glycerol ethoxylate triazide component of the hydrogel is a 3-arm glycerol ethoxylate triazide. In some embodiments, the multi-arm glycerol ethoxylate triazide component of the hydrogel is a 2-arm glycerol ethoxylate triazide.

The multi-arm glycerol ethoxylate triazide may have a molecular mass from about 500 Da to about 2,000 Da. In some embodiments, the multi-arm glycerol ethoxylate triazide may have a molecular mass from about 500 Da to about 1,000 Da. In some embodiments, the multi-arm glycerol ethoxylate triazide may have a molecular mass from about 1,000 Da to about 2,000 Da.

The azide end groups are connected to each other via a glycerol ethoxylate backbone, which may be of a linear, branched, or star shaped structure and comprises from 2 to about 5 arms comprised of from 8 to 30 ethylene glycol units. In some embodiments, each azide terminated arm has from about 8 to about 10 ethylene glycol units. In some embodiments, each azide terminated arm has from about 11 to about 20 ethylene glycol units. In some embodiment each azide terminated arm has from about 21 to about 30 ethylene glycol units.

As would be apparent to those of skill in the art, multi-arm glycerol ethoxylate triazide component of the hydrogel will be present in an aqueous solution. The concentration of the multi-arm glycerol ethoxylate triazide in water may be from about 1% to about 40%. In some embodiments, the multi-arm glycerol ethoxylate triazide is an aqueous solution comprising from about 1% to about 40% weight percent of a 3-arm glycerol ethoxylate triazide. In some embodiments, the multi-arm glycerol ethoxylate triazide is an aqueous solution comprising from about 1% to about 10% weight percent of a 3-arm glycerol ethoxylate triazide. In some embodiments, the multi-arm glycerol ethoxylate triazide is an aqueous solution comprising from about 11% to about 20% weight percent of a 3-arm glycerol ethoxylate triazide.

In some embodiments, the multi-arm glycerol ethoxylate triazide is an aqueous solution comprising from about 21% to about 30% weight percent of a 3-arm glycerol-ethoxylate triazide. In some embodiments, the multi-arm glycerol ethoxylate triazide is an aqueous solution comprising from about 31% to about 40% weight percent of a 3-arm glycerol ethoxylate triazide. In some embodiments, the multi-arm glycerol ethoxylate triazide is an aqueous solution comprising about 3% weight percent of a 3-arm glycerol ethoxylate triazide.

In some embodiments, the aqueous solution containing the multi-arm glycerol ethoxylate triazide component of the hydrogel further comprises an additive, which may be incorporated into and encapsulated by the hydrogel. Suitable additives include, but are not limited to, cells, collagen, decellularized tissue, gelatin, proteins, cell media, serum albumin, viruses, pharmaceutical compounds, enzymes, DNA, RNA, interfering RNA, other small biological agents, and combinations thereof. In some embodiments, the additive is encapsulated with said covalently crosslinked hydrogel.

In some embodiments, the multi-arm glycerol ethoxylate triazides component of the hydrogel may be a tri-arm PEG azide. In some embodiments, the multi-arm glycerol ethoxylate triazides has the structure of formula (ii).

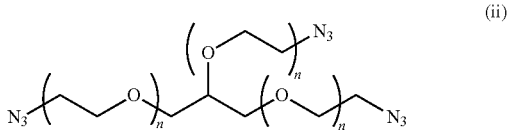

(ii)

wherein n is an integer from about 8 to about 30. In some embodiments, n is from about 8 to about 10. In some embodiments, n is from about 11 to about 20. In some embodiments, n is from about 21 to about 30.

In some embodiments, the multi-arm glycerol ethoxylate triazides component of the hydrogel may be a bi-arm PEG azide. In some embodiments, the multi-arm glycerol ethoxylate triazides has the structure of formula (iv).

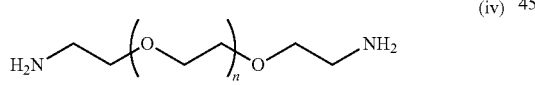

(iv)

wherein n is an integer from about 8 to about 30. In some embodiments, n is from about 8 to about 10. In some embodiments, n is from about 11 to about 20. In some embodiments, n is from about 21 to about 30.

As set forth above, the hydrogel of the present invention is comprised of the 8-member cycloalkyne functionalized polyalkylene glycols and multi-arm glycerol ethoxylate triazides discussed above, covalently crosslinked via strain-promoted azide-alkyne "click" cycloaddition reactions.

It has been found that the stoichiometric ratio of the 8-member cycloalkyne functionalized polyalkylene glycol component to the multi-arm glycerol ethoxylate triazide component in the hydrogel may affect its physical properties. If the stoichiometric ratio is not precise, the crosslink efficiency in the network will be reduced. The result will be dangling chain ends and a reduction in the mechanical properties. In some embodiments, the ratio may be from about 1:1 to about 2:3. In some embodiments, the ratio may be from about 1:1 to about 1:1.1. In some embodiments, the ratio may be from about 1:1.1 to about 1:1.2. In some embodiments, the ratio may be from about 1:1.2 to about 1:1.3. In some embodiments, the ratio may be from about 1:1.4 to about 2:3. A stoichiometric ratio of the 8-member cycloalkyne functionalized polyalkylene glycol component to the multi-arm glycerol ethoxylate triazide component is less than 1:1 will result in a lower extent of crosslinking and lower mechanical properties.

The covalently crosslinked hydrogel may be from about 40% to about 99.9% water. In some embodiments, the covalently crosslinked hydrogel may be from about 40% to about 60% water. In some embodiments, the covalently crosslinked hydrogel may be from about 61% to about 80% water. In some embodiments, the covalently crosslinked hydrogel may be from about 81% to about 90% water. In some embodiments, the covalently crosslinked hydrogel may be from about 90% to about 99.9% water. In some embodiments, the covalently crosslinked hydrogel is about 96.1% water.

As those of ordinary skill in the art will appreciate, the cross link density of the hydrogel will depend upon the length of the polyalkylene and glycerol ethoxylate chains and the concentration of the reagent mixture in solution. In some embodiments, the hydrogel has a crosslink density of from about 2 mol/m$^3$ to about 300 mol/m$^3$. In some embodiments, the hydrogel has a crosslink density of from about 10 mol/m$^3$ to about 200 mol/m$^3$. In some embodiments, the hydrogel has a crosslink density of from about 5 mol/m$^3$ to about 10 mol/m$^3$. In some embodiments, the hydrogel has a crosslink density of about 8.6 mol/m$^3$.

The loss factor (tan δ) for the polymer will depend upon the degree of crosslinking in the hydrogel and the molecular weights of the precursor polymers. In some embodiments, the hydrogel may have a loss factor (tan δ) of from about 0.10 to about 0.50. In some embodiments, the hydrogel has a loss factor (tan δ) of about 0.25.

In some embodiments, the hydrogel has the structure of formula (iii):

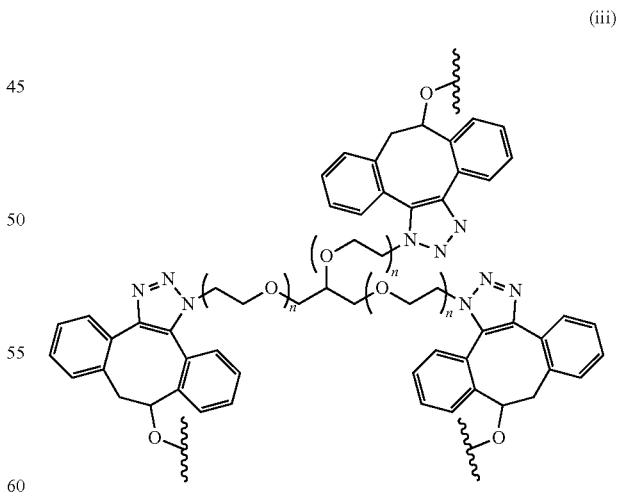

(iii)

wherein n is an integer from about 8 to about 30. In some embodiments, n is from about 8 to about 10. In some embodiments, n is from about 11 to about 20. In some embodiments, n is from about 21 to about 30.

As they crosslink, the 8-member cycloalkyne functionalized polyalkylene glycols and multi-arm glycerol ethoxylate triazides form a network. As should be apparent, this network comprises only from about 1% to about 40% of the hydrogel, with the rest being primarily water. As a result, there are a great number of spaces in and around this network within which various additives may be entrapped and transported by the hydrogel. The size and orientation of these spaces, among other factors such as the degree of crosslinking of the hydrogel and the molecular weights of the precursor polymers, will determine the size of the additives that may be entrapped and transported by the hydrogel and will be referred to herein broadly as the mesh size of the hydrogel. The mesh size is primarily a function of the molecular weight and concentration of the components used.

In some embodiments, the hydrogel further comprises one or more additive, which may be incorporated into and/or encapsulated by the hydrogel. Suitable additives include, but are not limited to, cells, collagen, decellularized tissue, gelatin, proteins, cell media, serum albumin, viruses, pharmaceutical compounds, enzymes, DNA, RNA, interfering RNA, other small biological agents, and combinations thereof. Which additives may be used with a particular hydrogel will primarily depend upon the mesh size of hydrogel and the size of the additive and the specific application being targeted.

The 8-member cycloalkyne functionalized polyalkylene glycol component of the present invention may be prepared by any method known or unknown in the art for that purpose. In some embodiments, the 8-member cycloalkyne functionalized polyalkylene glycol is a DIBO-functionalized PEG polymer and may synthesized from 4-nitrophenyl chloroformate activated 4-dibenzocyclooctynol and poly (ethylene gyclol) bis amine. $^1$H NMR and MALDI-TOF (FIG. 1) results demonstrate the complete conversion of the amine group to dibenzocyclooctynol.

Concentration and stoichiometric control are critical to achieving complete conversion. Too much or too little of either reagent will limit the extent of gelation and reduce the targeted mechanical properties.

In some embodiments, the 8-member cycloalkyne functionalized polyalkylene glycol is a DIBO-functionalized PEG polymer and may be synthesized as set forth below.

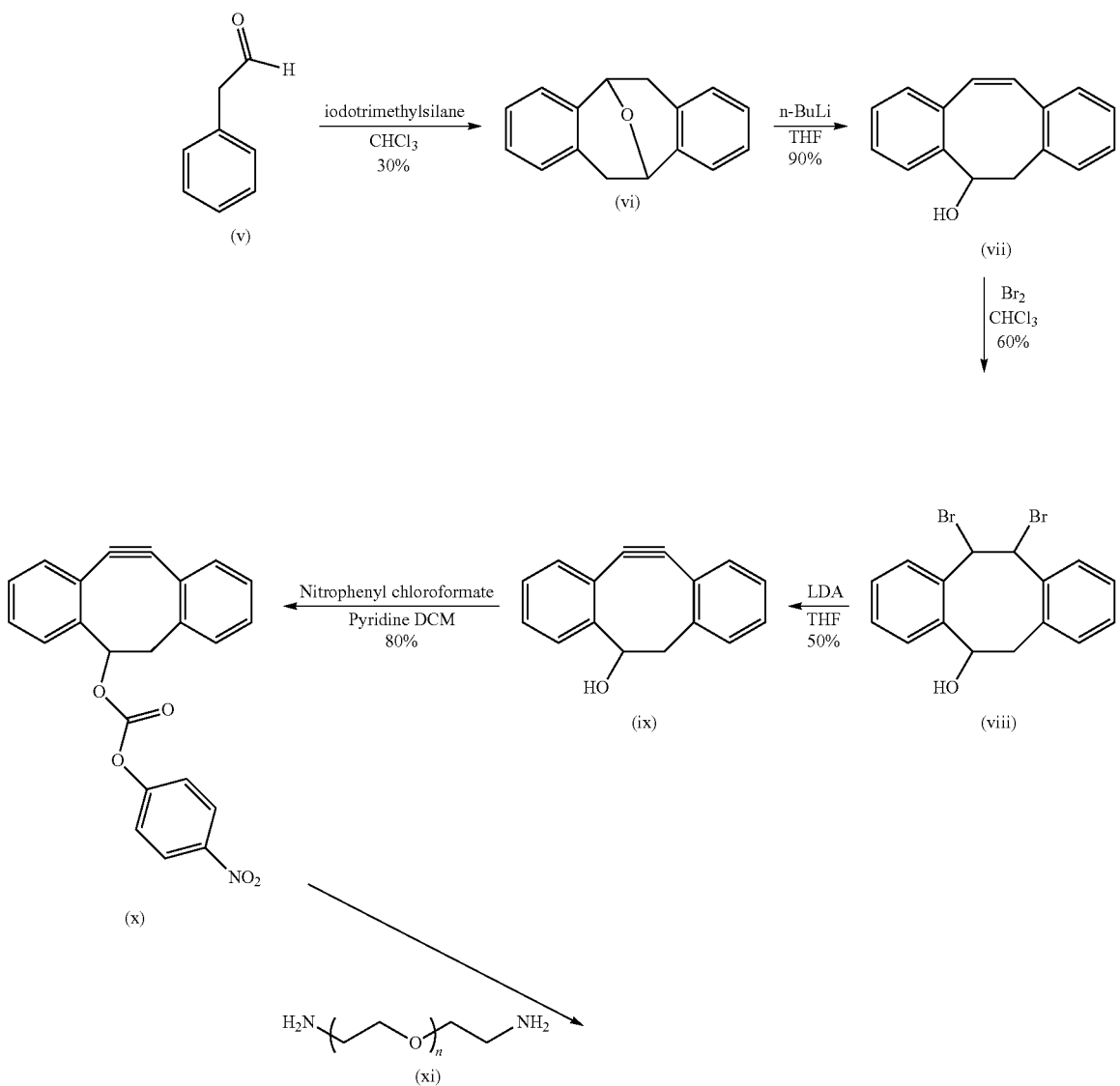

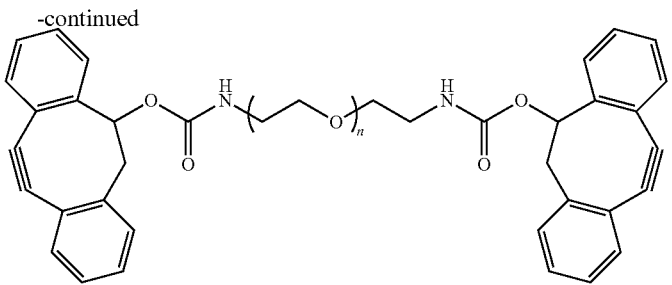

(i)

In some embodiments, phenylacetaldehyde (v) is reacted with iodotrimethylsilane in chloroform to form a 2,3:6,7-Dibenzo-9-oxabicyclo[3.3.1]nona-2,6-diene (vi) intermediate with a yield of approximately 30%. The 2,3:6,7-Dibenzo-9-oxabicyclo[3.3.1]nona-2,6-diene (vi) is then dissolved in THF and reacted with n-butyl lithium. The reaction was quenched with water and the product purified to produce a 3-Hydroxy-2',3',2",3"-tetramethoxly,-2:5,6-dibenzocyclocta-1,5,7-triene (vii) intermediate with a yield of approximately 90%.

The 3-Hydroxy-2',3',2",3"-tetramethoxly,-2:5,6-dibenzocyclocta-1,5,7-triene (vii) intermediary is then reacted with bromine in chloroform to produce the 11,12-Dibromo-5,6,11,12-tetrahydro-dibenzo[a,e]cycloocten-5-ol (viii) intermediary with a yield of approximately 60%. It is believed that yields of about 60% are significantly better than what has been reported and are likely the result of limiting the reaction time to approximately 30 minutes. It has been found that additional reaction time results in reduced yields.

The 11,12-Dibromo-5,6,11,12-tetrahydro-dibenzo[a,e]cycloocten-5-ol (viii) intermediary may then be reacted with lithium diisopropylamide in THF to produce the 5,6-Dihydro-11,12-didehydro-dibenzo[a,e]cycloocten-5-ol (ix) intermediary with a yield of approximately 50%. The 5,6-Dihydro-11,12-didehydro-dibenzo[a,e]cycloocten-5-ol (ix) intermediary may then be reacted with 4-nitrophenyl chloroformate and pyridine to produce the carbonic acid, 5,6-(dihydro-11,12-didehydro-dibenzo[a,e]cycloocten-5-yl ester, 4-nitrophenyl ester (x) intermediary. Finally the carbonic acid, 5,6-(dihydro-11,12-didehydro-dibenzo[a,e]cycloocten-5-yl ester, 4-nitrophenyl ester (x) intermediary may be reacted with polyethylene glycol bisamine (xi) to for dibenzylcyclooctyne Polyethylene glycol (i).

Figure 2:
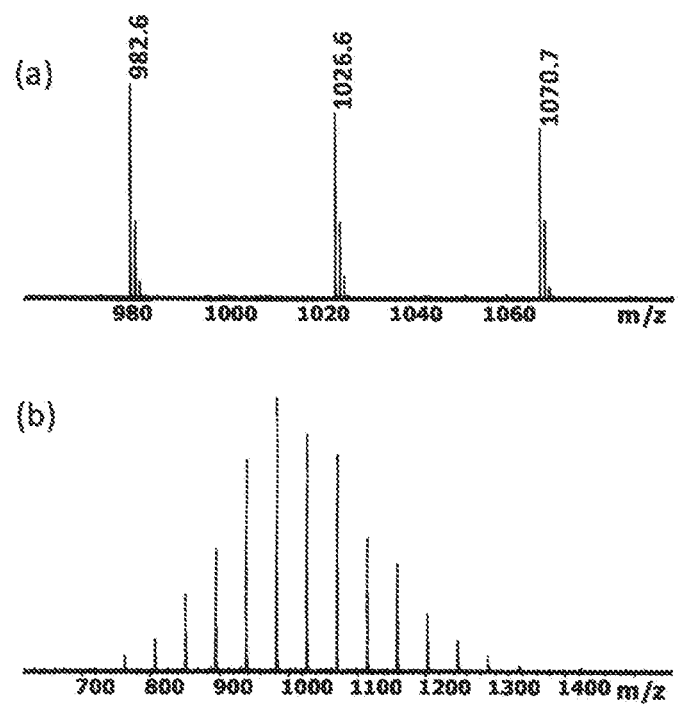
FIG. 2 is a MALDI-TOF mass spectrum of glycerol ethoxylate triazide (cationized with NaTFA) made according to at least one embodiment of the present invention. Monoisotopic mass-to-charge ratios (m/z) are marked in the upper spectrum. The measured m/z values agree with the anticipated structure.

The multi-arm glycerol ethoxylate triazide component of the present invention may be prepared by any method known or unknown in the art for that purpose. In some embodiments, the multi-arm glycerol ethoxylate triazide may be synthesized using glycerol ethoxylate as the starting material. The hydroxyl groups are then derivatized with methane sulfonyl chloride and further substituted using sodium azide in a two-step process. The desired product may then be purified by column chromatography and substantiated with $^1$H NMR and MALDI-TOF. See FIG. 2.

Figure 3:
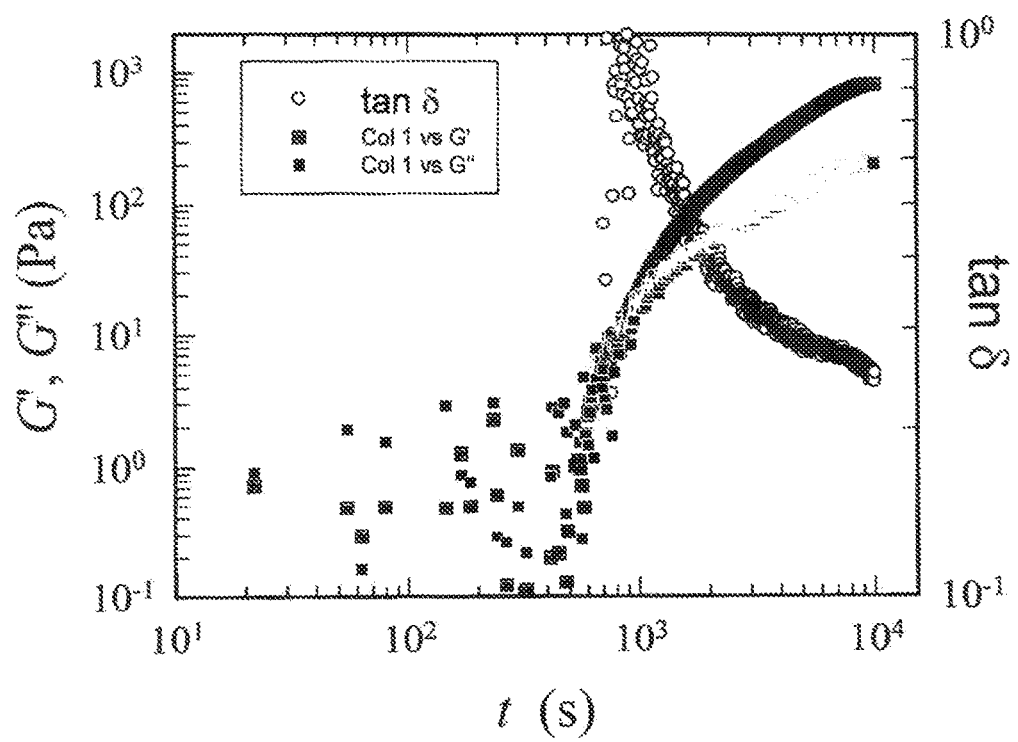
FIG. 3 is a graph showing the modulus-time dependence of hydrogels according to at least one embodiment of the present invention during the process of oscillation shear.

In general outline, the hydrogels of the present invention may be made as follows. The aqueous 8-member cycloalkyne functionalized polyalkylene glycol and aqueous multi-arm glycerol ethoxylate triazide solutions discussed above are prepared separately and combined to form a viscous liquid. Prior to crosslinking, the mixture of the two precursor solutions will have a loss factor (tan δ) greater than or equal to about 1.0, and preferably is about 1.0, which is typical of a viscous liquid. A strain is then applied to the mixture, causing it to crosslink to form a hydrogel. Once crosslinked, the hydrogel may have a loss factor (tan δ) of from about 0.10 to about 0.50, which is typical for a viscoelastic solid. In some embodiments, the hydrogel has a loss factor (tan δ) of about 0.25. See FIG. 3.

In some embodiments, the hydrogel crosslinks as set forth below:

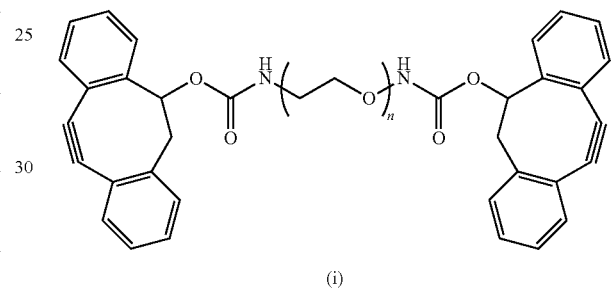

(i)

+

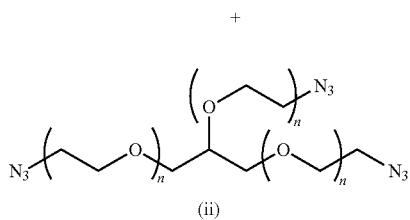

(ii)

↓

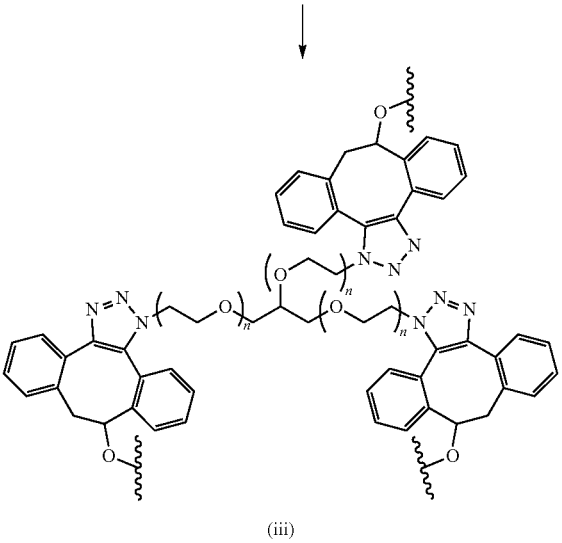

(iii)

As set forth above, the crosslinking reaction is strain induced. It is believed that the strain provides sufficient energy to initiate the reaction. The precursor compounds may be mixed and will not crosslink until the strain applied to the mixture reaches the strain point. As used herein, the strain point refers to the amount of strain necessary for the reaction components to begin to crosslink. As those of ordinary skill in the art will recognize, this will occur at the point at which the loss modulus for the hydrogel (G") equals the storage modulus for the hydrogel (G') as set forth in FIG. 3.

Suitable types of strain include, but are not limited to, oscillatory and linear shear strain. In some embodiments, the strain applied may be is an oscillatory shear strain of from about 5% to about 15%. In some embodiments, the strain applied may be is an oscillatory shear strain of from about 10% to about 15%. In some embodiments, the strain applied may be is a 10% oscillatory shear strain.

In determining an appropriate strain to use for a given application, several factors should be considered in addition to the strain point of the reaction mixture. First, the nature of any additives being encapsulated into the hydrogel should be considered. If the strain rate or amplitude is too high, sensitive cells and other biological materials may be damaged or destroyed. Second, it has been found that the rate of network formation can be influenced by the rate and amplitude of the oscillatory sheer strain of the amount of linear shear strain. If the rate and/or amplitude of strain are too high, crosslinking may occur prematurely, for example, within a syringe administering the hydrogel to a patent.

As will be appreciated by those of skill in the art, the speed of the crosslinking reaction may also be temperature dependent. In general and with all other factors being equal, the speed of the click reaction will increase with the temperature. One advantage of the present method is that, for most embodiments, the reaction can occur at both at room temperature and at the body temperature of humans and most warm blooded animals. It is important that the reaction temperature not be so high as to damage any cells or other sensitive additives being encapsulated into the hydrogel and it is believed that these temperatures, from about 15° C. to about 43° C. are safe for most additives. It should also be recognized that an elevated temperature will exacerbate the premature crosslinking issue discussed above.

In some embodiments, the crosslinking temperature is from about 15° C. to about 43° C. In some embodiments, the crosslinking temperature is from about 20° C. to about 42° C. In some embodiments, the crosslinking temperature is from about 23° C. to about 37° C. In some embodiments, the crosslinking temperature is from about 23° C. to about 25° C. In some embodiments, the crosslinking temperature is from about 37° C. to about 42° C.

In some embodiments, the hydrogel components may be injected into a subject and crosslinked in vivo. In some embodiments, the aqueous 8-member cycloalkyne functionalized polyalkylene glycol and aqueous multi-arm glycerol ethoxylate triazide solutions are combined in a standard syringe and injected into the subject. In some embodiments, a duel chamber syringe with the aqueous 8-member cycloalkyne functionalized polyalkylene glycol and aqueous multi-arm glycerol ethoxylate triazide solutions in separate chambers may be used. In these embodiments, the solutions are combined as they are injected into the subject. The injection provides sufficient strain to initiate the crosslinking reaction and the hydrogel is formed in-vivo.

In some embodiments, the method of the present invention may include entrapping and/or encapsulating an additive within the hydrogel. As set forth above, suitable additives include, but are not limited to, cells, collagen, decellularized tissue, gelatin, proteins, cell media, serum albumin, viruses, pharmaceutical compounds, enzymes, DNA, RNA, interfering RNA, other small biological agents, and combinations thereof. The additive may be added to either precursor solution at any time prior to crosslinking, but should be added before the two precursor solutions are mixed to prevent the addition of the additive from initiating the crosslinking reaction. As set forth above, the particular additives which may be used with a particular hydrogel will primarily depend upon the mesh size of hydrogel and the size of the additive.

When used as scaffolds in tissue engineering, hydrogels of the present invention may contain human cells in order to repair tissue. Some environmentally sensitive embodiments of the novel hydrogels may have the ability to sense changes of pH, temperature, or the concentration of metabolite and release their load as result of such a change. As dressings for burns or other hard-to-heal wounds, these hydrogels may be excellent for helping to create or maintain a wound environment. Hydrogels that are responsive to specific molecules, such as glucose or antigens, may be used as biosensors as well as in drug delivery systems.

Hydrogels of the present invention may also been used as reservoirs in topical drug delivery, particularly for the delivery of ionic drugs. As set forth above, the mechanical properties can be precisely controlled due to the nature of the chemical reaction and there are no residual molecules released in solution. The release rates can be changes by modifying the molecular mass of the individual components which determine the mesh size. Due to the nature of the crosslinking chemistry, the mesh size and resulting transport properties may be tightly controlled and highly reproducible relative to radically initiated crosslinked gels or physically crosslinked gels.

Various aspects of the present invention have been described herein as a range from a first end point value to a second end point value. It should be understood that the first and second end point values are intended be included within the disclosed range.

In light of the foregoing, it should be appreciated that the present invention significantly advances the art by providing a covalently crosslinked hydrogel that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

General Methods and Materials

Unless otherwise specified, chemicals and solvents were purchased from Sigma-Aldrich and Acros and were used without further purification. All reactions were performed in anhydrous conditions under an atmosphere of Argon. Flash chromatography was performed on silica gel (Sorbent Technologies Inc., 70-230 mesh). $^1$H and $^{13}$C NMR spectra were acquired using a Varian NMRS 500 and Varian NMRS 300. FTIR spectra were acquired using a FTIR-ATR MIRacle 10 SHIMADZU spectrometer.

ESI MS was performed on a Waters Synapt HDMS quadrupole/time-of-flight (Q/ToF) instrument. The sprayed solution was prepared by dissolving sample in chloroform/methanol (1/1) containing 1% NaTFA (1 mg/mL in methanol) solution. The following ESI parameters were selected: ESI capillary voltage, 3.5 kV; sample cone voltage, 35 V; extraction cone voltage, 3.2 V; desolvation gas flow, 500 L/h (N2); trap collision energy (CE), 6 eV; transfer CE, 4 eV; trap gas flow, 1.5 mL/min (Ar); sample flow rate, 5 μL/min; source temperature, 80° C.; desolvation temperature, 150° C.

MALDI-TOF mass spectra were acquired with a Bruker Ultraflex-III TOF/TOF mass spectrometer (Bruker Daltonics, Inc., Billerica, Mass.) equipped with a Nd:YAG laser (355 nm). All spectra were measured in positive reflection mode. The instrument was calibrated using external polystyrene or PMMA standards at the molecular weight under consideration. A solution of trans-2-[3-(4-tert-butylphenyl)-2-methyl-2-propenylidene]-malononitrile (DCTB, Santa Cruz Biotechnology, Inc., >99%) which was used as matrix was prepared in CHCl3 at a concentration of 20 mg/mL. Solutions of sodium trifluoroacetate or silver trifluoroacetate, which were used as cationizing salt, were prepared in MeOH/CHCl3 (v/v=1/3) at a concentration of 10 mg/mL. All the samples were dissolved in CHCl3. Matrix and cationizing salt were mixed in a ratio of 10/1 (v/v). The sample preparation involved depositing 0.5 μL of matrix and salt mixture on the wells of a 384-well ground-steel plate, allowing the samples to air-dry, depositing 0.5 μL of sample on the matrix spot, and adding another 0.5 μL of matrix and salt mixture on the dry sample spot. After evaporation of solvent, the target plate was inserted into the MALDI source. The laser was adjusted and attenuated to minimize undesired polymer fragmentation and to optimize the peak intensity.

Example 1

Synthesis of 4-dibenzocyclooctynol

The synthesis of 4-dibenzocyclooctynol is based on methods described previously in Jung, M. E.; Mossman, A. B.; Lyster, M. A. *J. Org. Chem.* 1978, 43, 3698; Ning, X.; Guo, J.; Wolfert, M. A.; Boons, G.-J. *Angew. Chem. Int. Ed.* 2008, 47, 2253; and Mbua, N. E.; Guo, J.; Wolfert, M. A.; Steet, R.; Boons, G. J. *chembiochem* 2011, 12, 1912, the disclosures of which are incorporated herein by reference in their entirety.

Example 2

Synthesis of 2,3:6,7-Dibenzo-9-oxabicyclo [3.3.1]nona-2, 6-diene (vi)

Figure 4A:
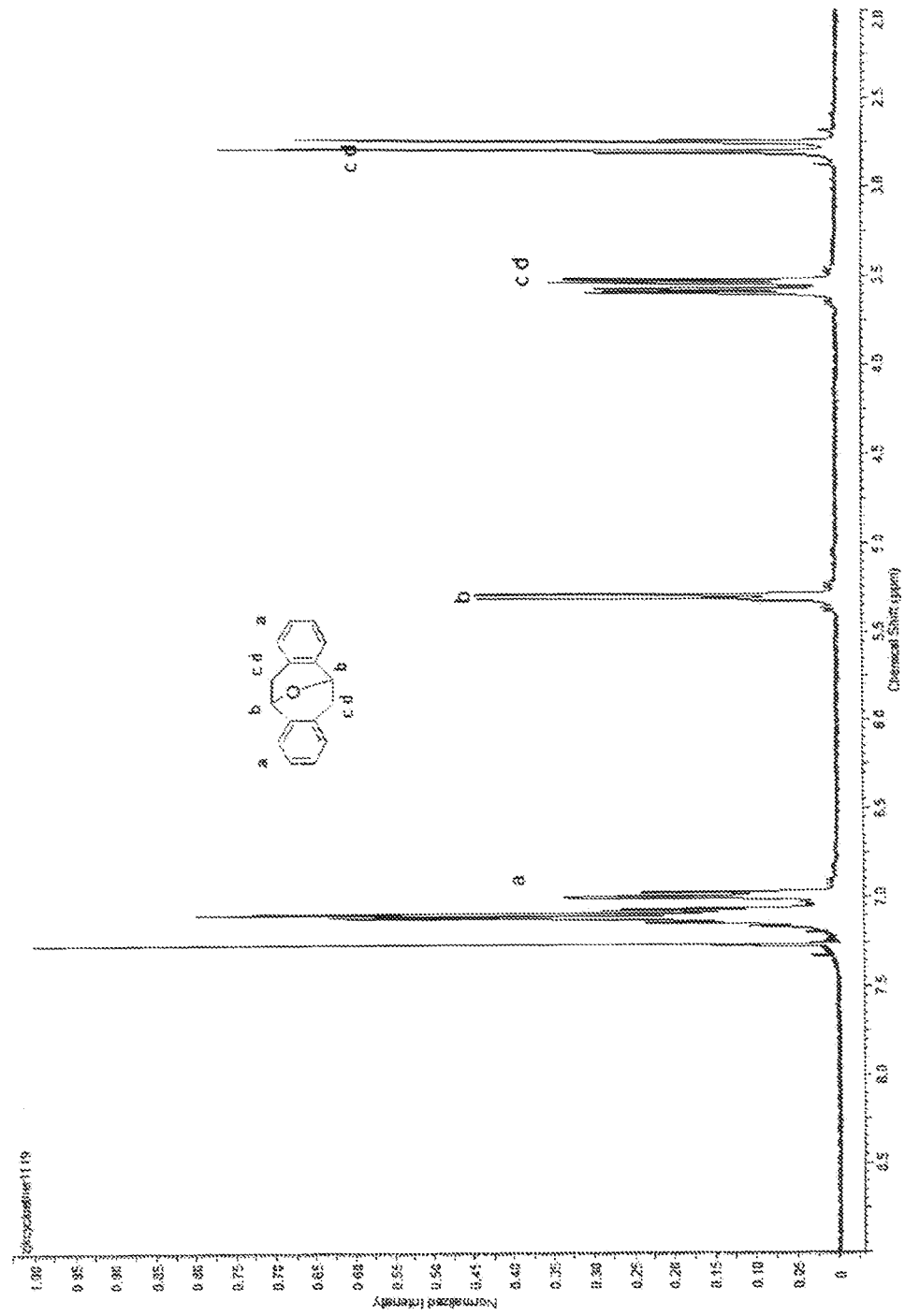
FIGS. 4A and 4B are $^1$H NMR and $^{13}$C NMR spectra of 2,3:6,7-Dibenzo-9-oxabicyclo[3.3.1]nona-2,6-diene (vi).
Figure 4B:
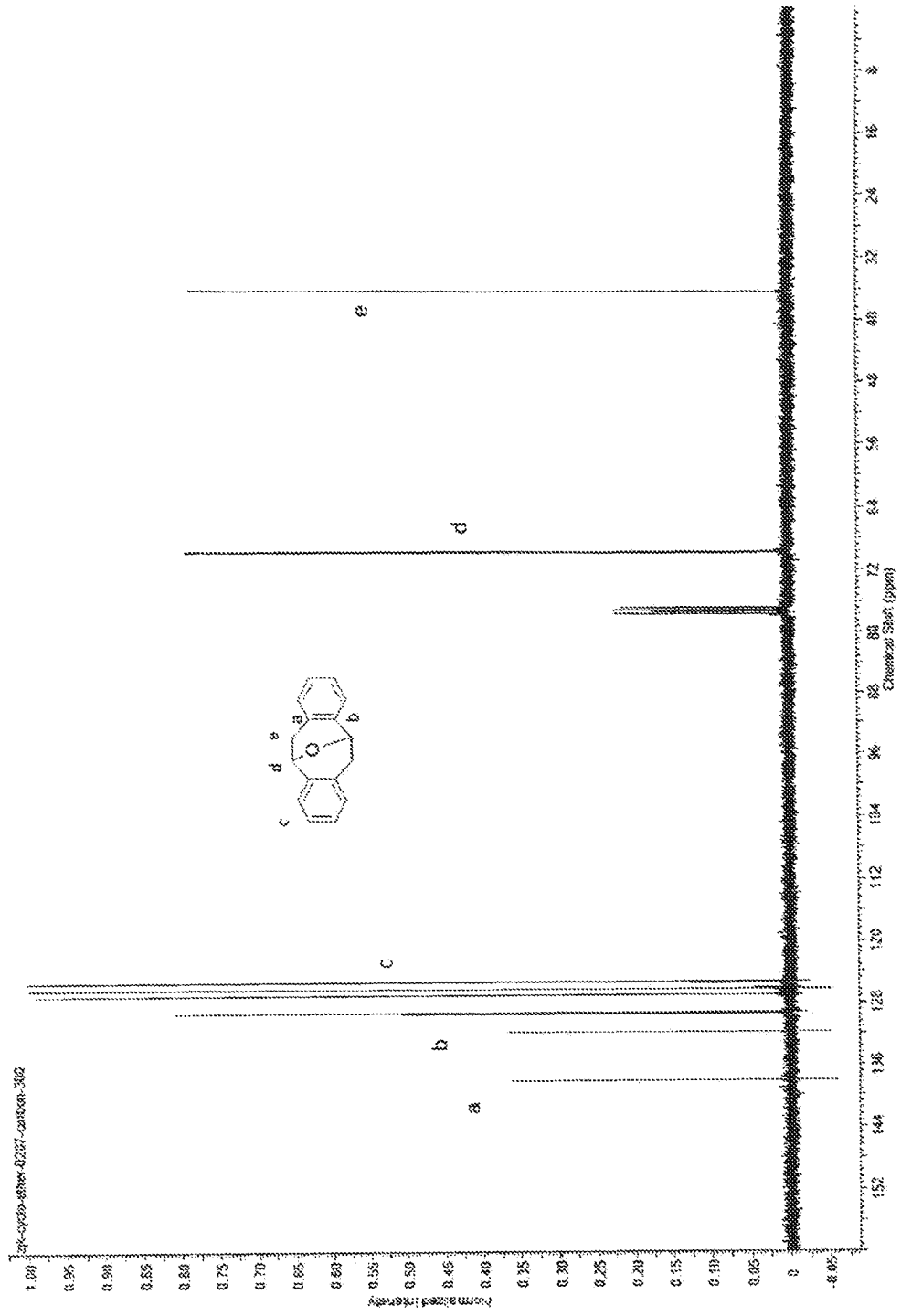

A 250 mL flask was flame dried and charged with argon. Phenylacetaldehyde (18.52 g, 0.154 mol) and 100 mL of chloroform (anhydrous) were then added via syringe. The reaction flask was cooled in an ice bath. Trimethylsilyl iodide (25 mL, 37.5 g, 0.188 mol) was added to the solution and the reaction was allowed to stand at 5° C. for 7 days. The reaction was monitored by thin layer chromatography. After 7 days, sodium thiosulfate (1.0 M, 160 mL) and chloroform (200 mL) were added, and the mixture was stirred until the iodine color was discharged. The organic phase was separated, dried (sodium sulfate), and concentrated in vacuum. Chromatography on silica gel eluting with chloroform yielded 6.1 g of the crystalline ether compound (35%). The $^1$H NMR and $^{13}$C NMR spectra for the reaction product are attached as FIGS. 4A and 4B. The results of the $^1$H NMR and $^{13}$C NMR were as follows: $^1$H NMR (300 MHz, CDCl$_3$) δ=7.09 (m, 8H), 5.30 (d, 2H, J=5.9 Hz, CH), 3.55 (dd, 2H, J=6.3, 16.2 Hz, CH$_2$), 2.75 (d, 2H, J=16.4 Hz, CH$_2$); $^{13}$C NMR (300 MHz, CDCl$_3$) δ=137.98, 131.79, 129.28, 127.02, 126.16, 125.35, 69.75, 36.31. ESI MS m/z 245.1334 [M+Na+]; calculated for C$_{16}$H$_{14}$NaO+: 245.0942.

Example 3

Synthesis of 3-Hydroxy-2',3',2",3"-tetramethoxly,-2:5,6-dibenzocyclocta-1,5,7-triene (vii)

2,3:6,7-Dibenzo-9-oxabicyclo[3.3.1]nona-2,6-diene (vi) of Example 2 (2.00 g, 5.84 mmol) in anhydrous THF (60 mL) was placed into a three-necked round bottom flask and cooled in an ice bath under argon, n-butyl lithium (4.92 mL, 2.5 M, 12.4 mmol) was added slowly via syringe. The reaction mixture was stirred at room temperature under argon for 4 hours. The reaction was quenched by careful addition of water and extracted with 2×50 mL CHCl$_3$. The combined organic phases were washed with 30 mL of brine, dried over Na$_2$SO$_4$, concentrated under vacuum and purified by column chromatography on silica gel CHCl$_3$ to yield 1.83 g of 3-Hydroxy-2',3',2",3"-tetramethoxly,-2:5,6-dibenzocyclocta-1,5,7-triene (vii) (90%).

Figure 5A:
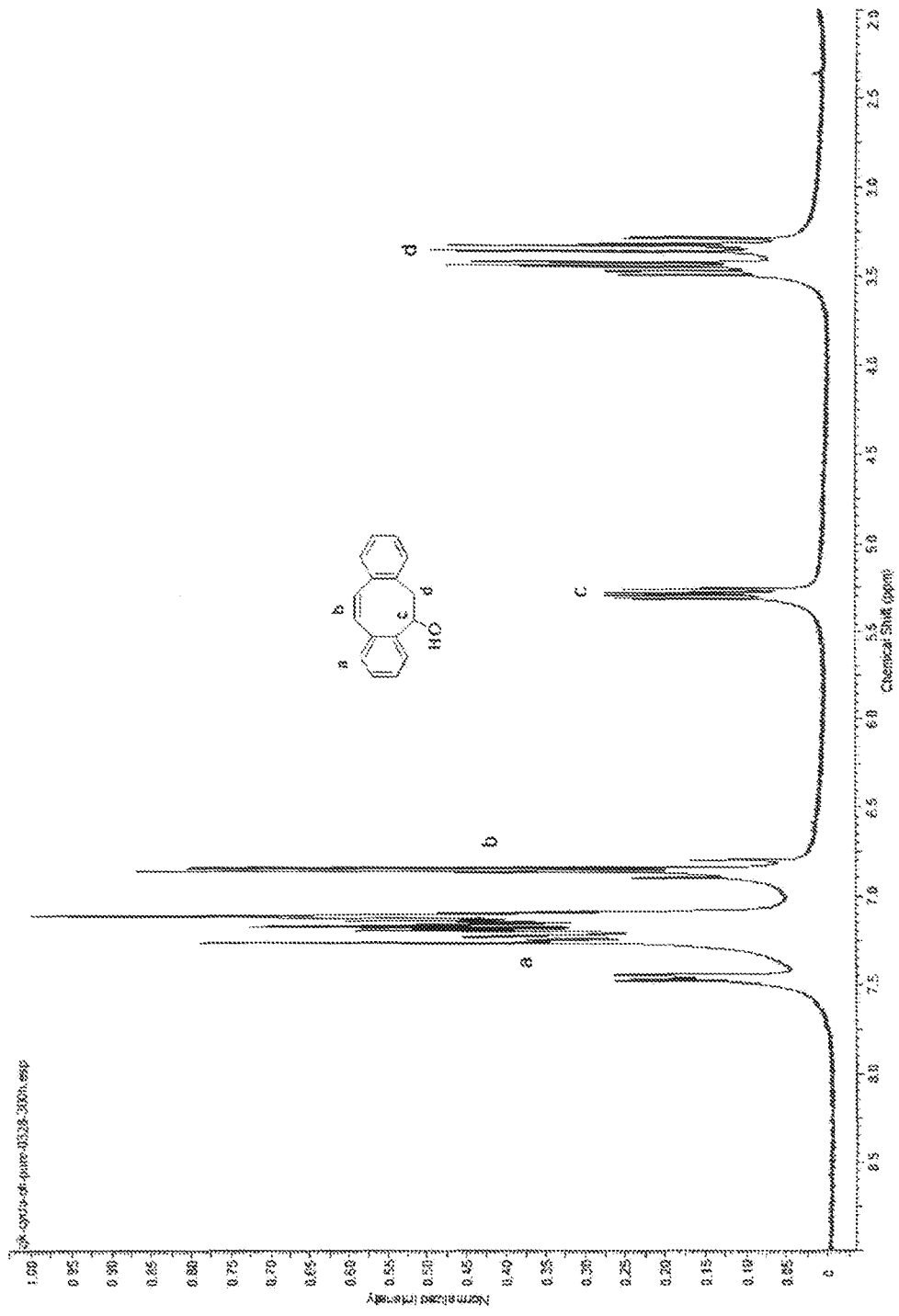
FIGS. 5A and 5B are $^1$H NMR and $^{13}$C NMR spectra of 3-Hydroxy-2',3',2'',3''-tetramethoxly,-2:5,6-dibenzocyclocta-1,5,7-triene (vii).
Figure 5B:
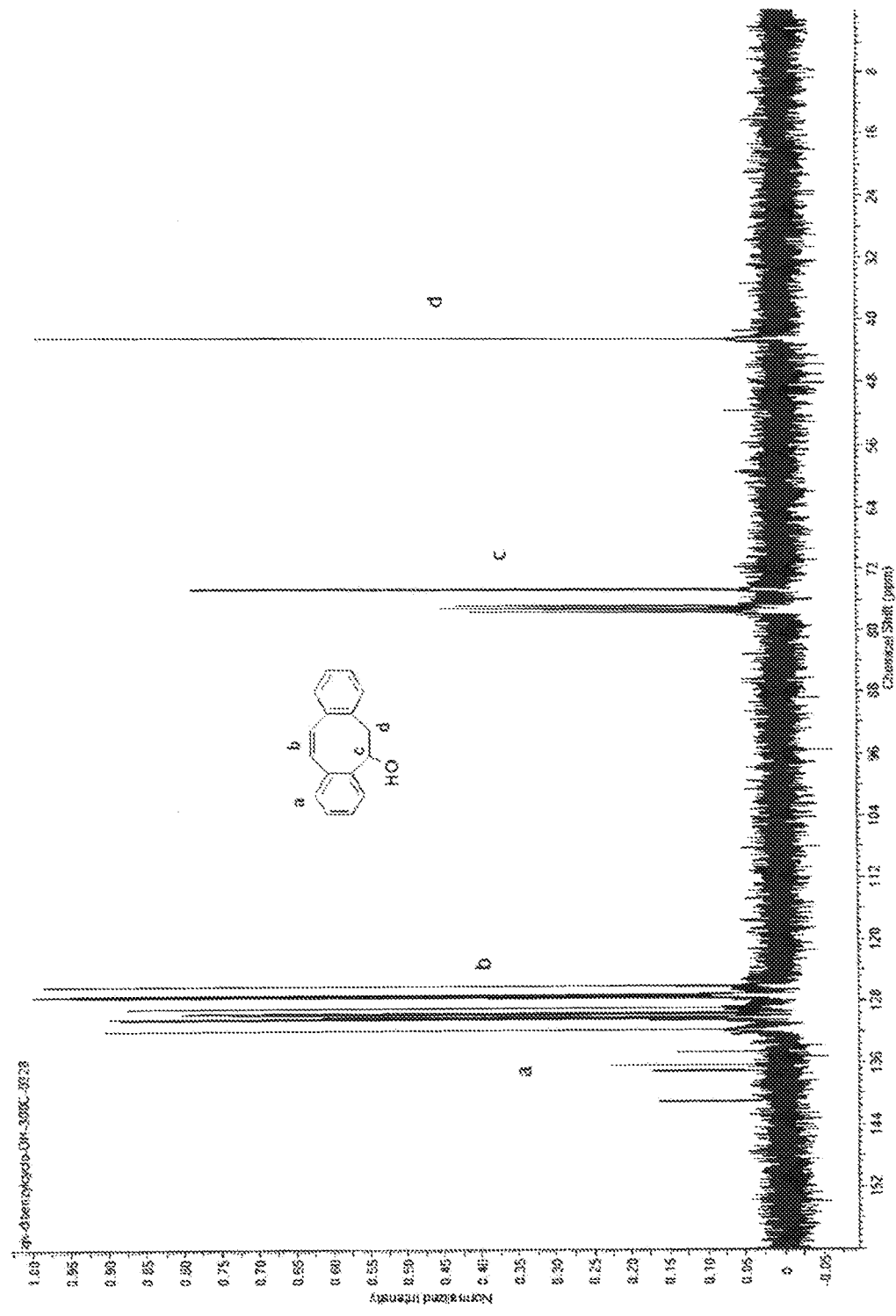

The $^1$H NMR and $^{13}$C NMR spectra for the reaction product (vii) are attached as FIGS. 5A and 5B. The results of the $^1$H NMR and $^{13}$C NMR were as follows: $^1$H NMR (300 MHz, CDCl$_3$): δ=7.48 (m, 1H), 7.10-7.30 (m, 7H), 6.86 (q, 2H, J=2.7, 12.0 Hz, CH), 5.31 (q, 1H, J=6.1, 10.0 Hz, CHOH), 3.45 (m, 2H, CH$_2$); $^{13}$C NMR (300 MHz, CDCl$_3$): d=140.9, 136.9, 136.3, 134.6, 131.8, 131.7, 130.3, 129.9, 129.3, 128.8, 127.3, 127.2, 126.1, 125.9, 74.7, 42.7. ESI MS m/z 245.1277 [M+Na$^+$]; calcd for C$_{16}$H$_{14}$NaO$^+$: 245.0942.

Example 4

Synthesis of 11,12-Dibromo-5,6,11,12-tetrahydro-dibenzo[a,e]cycloocten-5-ol (viii)

Figure 6A:
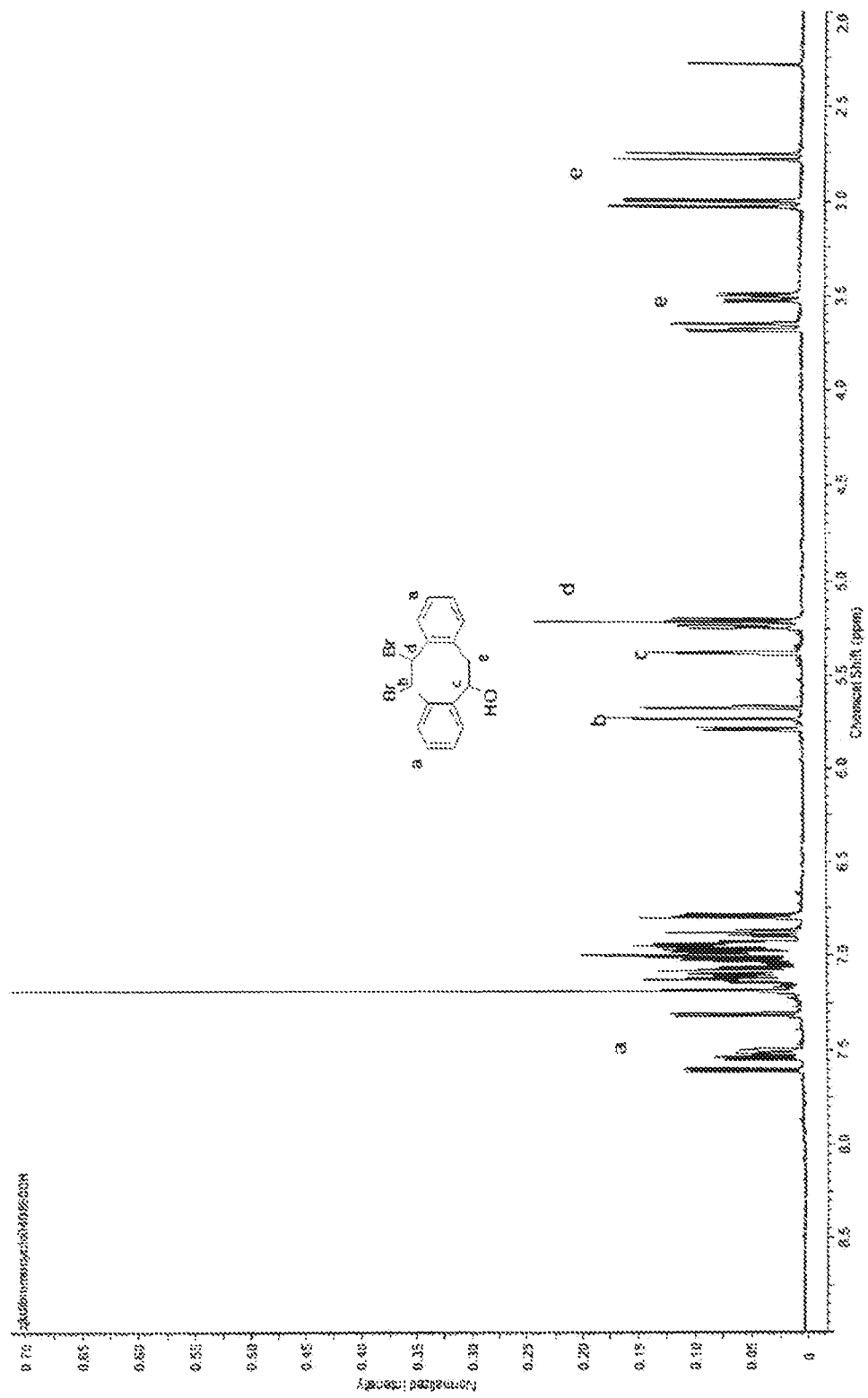
FIGS. 6A and 6B are $^1$H NMR and $^{13}$C NMR spectra of 11,12-Dibromo-5,6,11,12-tetrahydro-dibenzo[a,e]cycloocten-5-ol (viii).
Figure 6B:
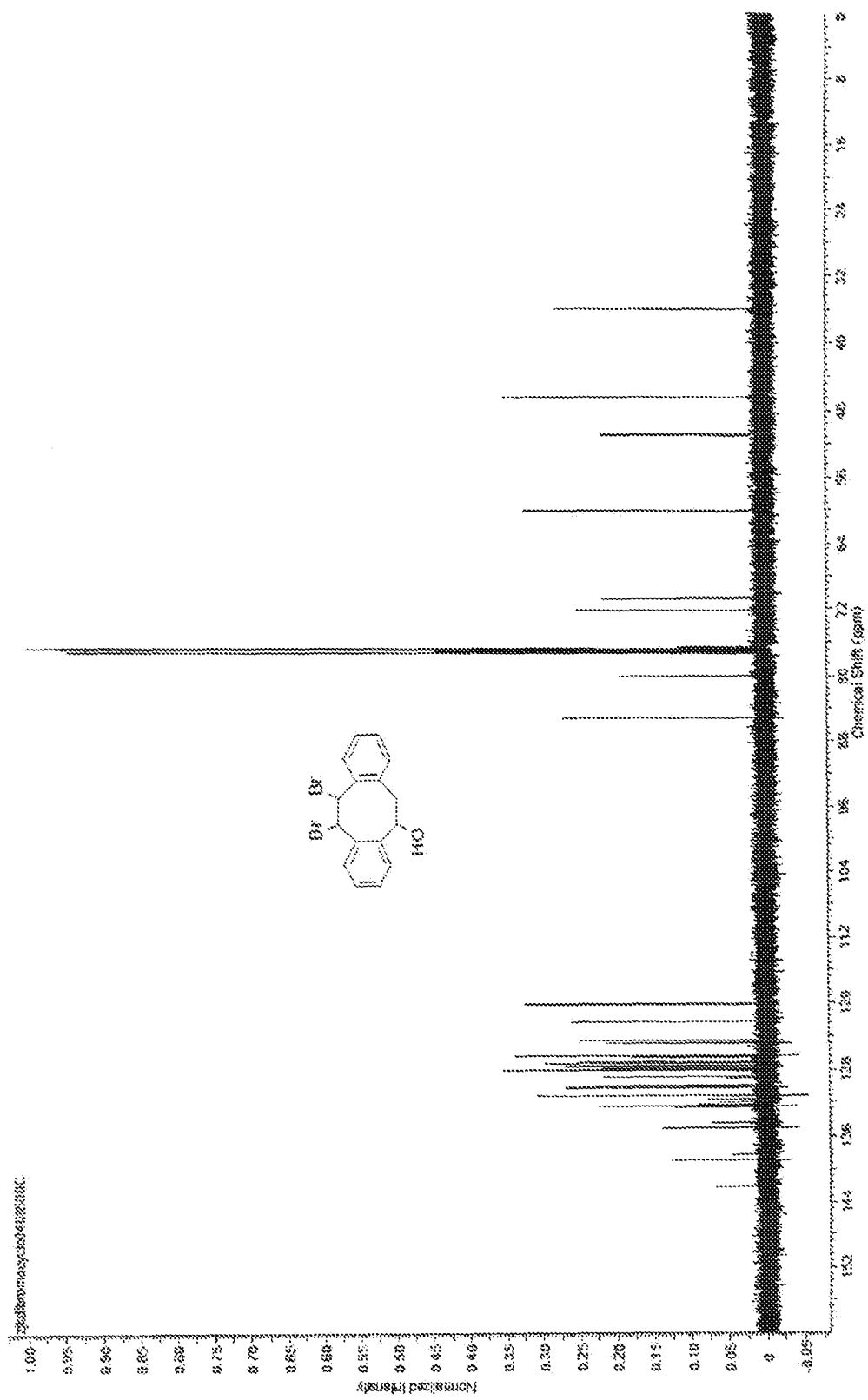

Bromine (0.51 mL, 10 mmol) was added dropwise to a stirred solution of compound (vii) (prepared as set forth above in Example 3) (2.22 g, 10 mmol) in CHCl$_3$ (50 mL). After stirring the mixture for 0.5 hours, thin layer chromatography (TLC) analysis indicated completion of the reaction. The solvent was evaporated under reduced pressure and the residue was purified by flash chromatography over silica gel (2:1/1:2, v/v, hexanes/CH$_2$Cl$_2$) to yield 11,12-Dibromo-5,6,11,12-tetrahydro-dibenzo[a,e]cycloocten-5-ol (viii) as a light-yellow oil (60%). The $^1$H NMR and $^{13}$C NMR spectra for the reaction product are attached as FIGS. 6A and 6B. The results of the $^1$H NMR and $^{13}$C NMR were as follows: $^1$H NMR (500 MHz, CDCl$_3$): δ=7.70-7.68 (2H, aromatics), 7.39-6.88 (6H, aromatics), 5.88 (d, 1H, J=5.4 Hz, CHBr), 5.47 (dd, 1H, J=3.6, 15.9 Hz, CHOH), 5.30 (d, 1H, J=5.4 Hz, CHBr), 3.60 (dd, 1H, J=3.7, 16.1 Hz, $CH_2$), 2.87 (dd, 1H, J=3.7, 16.1 Hz, $CH_2$); $^{13}C$ NMR (500 MHz, $CDCl_3$): δ=142.2, 138.9, 138.2, 135.0, 134.3, 132.5, 132.3, 131.1, 128.8, 127.2, 124.7, 122.3, 80.3, 70.6, 60.1 36.0. ESI MS m/z 402.9749 [M+Na$^+$]; calcd for $C_{16}H_{14}Br_2NaO^+$: 402.9309.

Example 5

Synthesis of 5,6-Dihydro-11,12-didehydro-dibenzo [a,e]cycloocten-5-ol (ix)

Figure 7A:
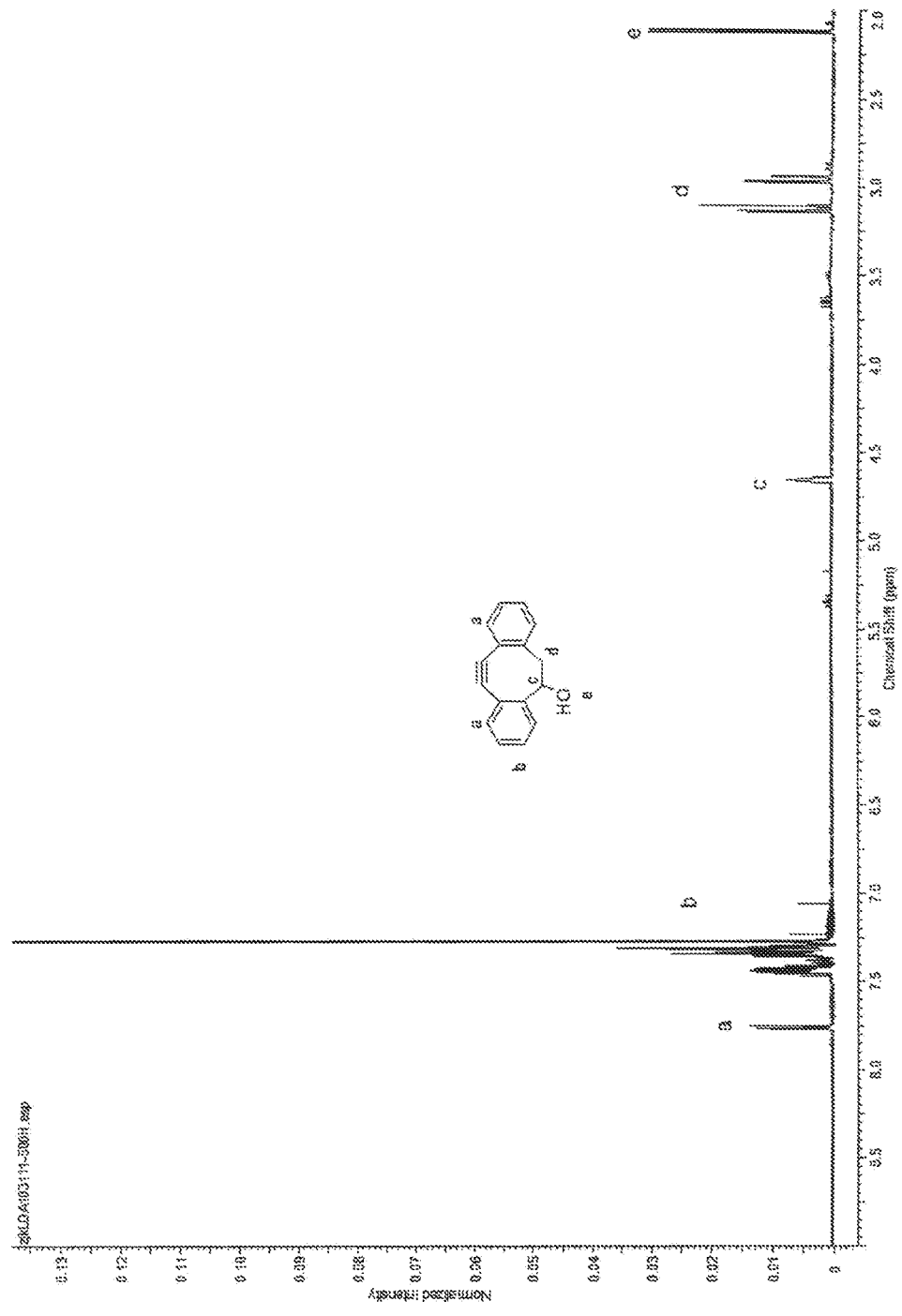
FIGS. 7A and 7B are $^1$H NMR and $^{13}$C NMR spectra of 5,6-Dihydro-11,12-didehydro-dibenzo[a,e]cycloocten-5-ol (ix)
Figure 7B:
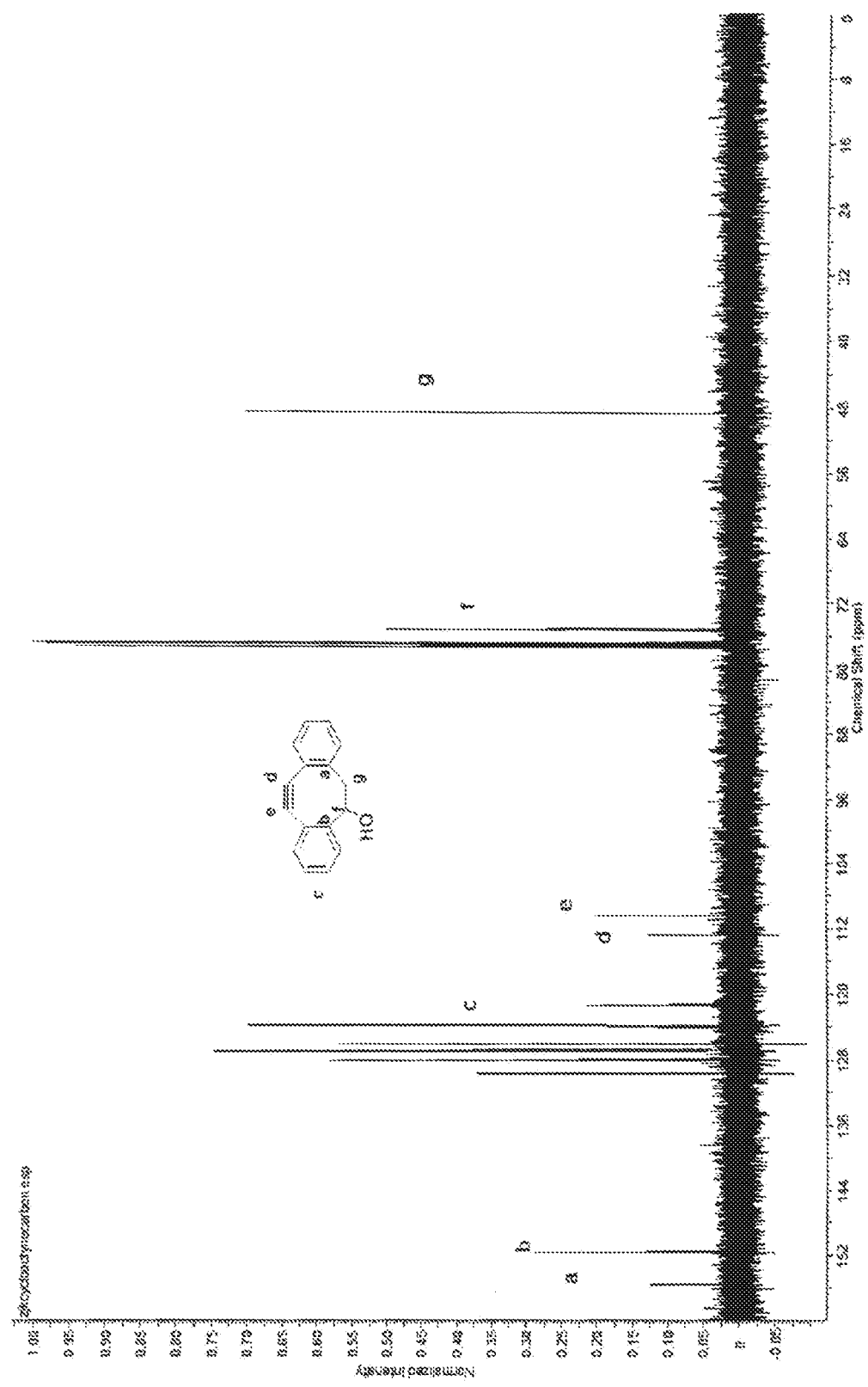

Lithium diisopropylamide in tetrahydrofuran (2.0 M; 8.0 mL, 16 mmol) was added dropwise to a stirred solution of 11,12-Dibromo-5,6,11,12-tetrahydro-dibenzo[a,e]cycloocten-5-ol (viii) (prepared as set forth above in Example 4) (1.53 g, 4.0 mmol) in tetrahydrofuran (40 mL) under an atmosphere of argon. The reaction mixture was stirred for 0.5 h, after which it was quenched by the dropwise addition of water (0.5 mL). The solvents were removed under reduced pressure, and the residue was purified by flash chromatography on silica gel (hexanes/$CH_2Cl_2$ 2:1/0:1, v/v) to yield 5,6-Dihydro-11,12-didehydro-dibenzo[a,e]cycloocten-5-ol (ix) as a white amorphous solid (0.52 g, 60%). %). The $^1H$ NMR and $^{13}C$ NMR spectra for the reaction product (ix) are attached as FIGS. 7A and 7B. The results of the $^1H$ NMR and $^{13}C$ NMR were as follows: $^1H$ NMR (500 MHz, $CDCl_3$): δ=7.77 (1H, aromatics), 7.44-7.23 (7H, aromatics), 4.66 (dd, J=2.1, 14.7 Hz, 1H, CHOH), 3.10 (dd, J=2.1, 14.8 Hz, 1H, $CH_2$), 2.94 (dd, J=2.1, 14.8 Hz, 1H, $CH_2$); $^{13}C$ NMR (500 MHz, $CDCl_3$): δ=155.5, 151.6, 129.6, 128.0, 127.9, 126.9, 126.8, 126.1, 124.7, 124.0, 123.7, 121.2, 112.9, 110.6, 75.2, 48.7. ESI MS m/z 243.1162 [M+Na$^+$]; calcd for $C_{16}H_{12}NaO^+$:243.0786.

Example 6

Synthesis of carbonic acid, 5,6-(dihydro-11, 12-didehydro-dibenzo[a,e]cycloocten-5-yl ester, 4-nitrophenyl ester (x)

Figure 8A:
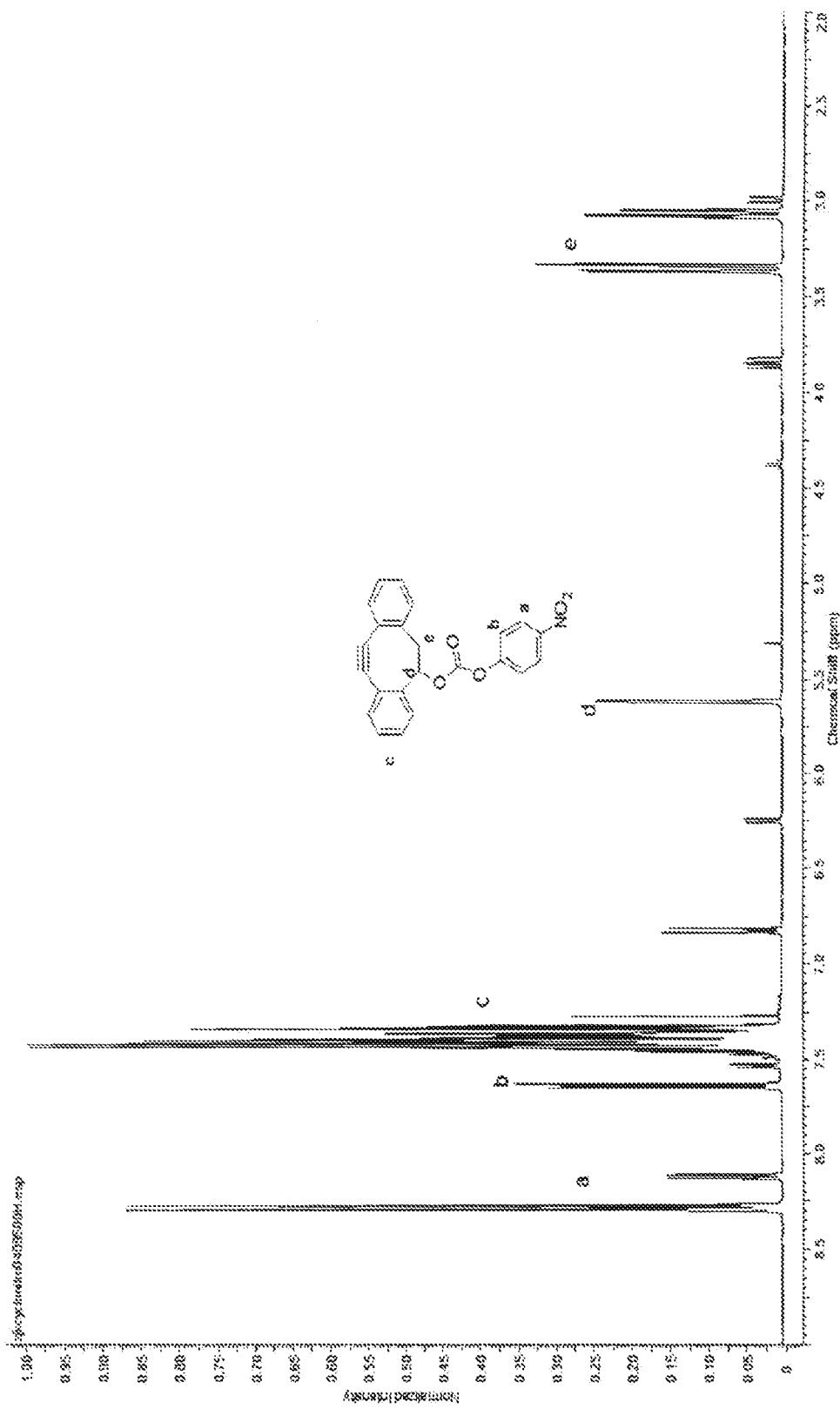

4-Nitrophenyl chloroformate (0.4 g, 2 mmol) and pyridine (0.4 mL, 5 mmol) were added to a solution of 5,6-Dihydro-11,12-didehydro-dibenzo[a,e]cycloocten-5-ol (ix) (prepared as set forth above in Example 5) (0.22 g, 1 mmol) in $CH_2Cl_2$ (30 mL). After being stirred for 4 hours at room temperature, the mixture was washed with brine (2×10 mL) and the organic layer was dried ($MgSO_4$). The solvents were evaporated under reduced pressure, and the residue was purified by silica gel column chromatography (hexane/ethyl acetate, 10:1, v/v) to afford carbonic acid, 5,6-(dihydro-11,12-didehydro-dibenzo[a,e]cycloocten-5-yl ester, 4-nitrophenyl ester (x) (0.32 g, 82%). The $^1H$ NMR and $^{13}C$ NMR spectra for the reaction product (x) are attached as FIGS. 8A and 8B. The results of the $^1H$ NMR and $^{13}C$ NMR were as follows: $^1H$ NMR (500 MHz, $CDCl_3$): δ=8.28-8.14 (2H, aromatics), 7.64-7.63 (2H, aromatics), 7.45-7.23 (8H, aromatics), 5.61 (dd, J=3.9, 15.3 Hz, 1H, CHOH), 3.37 (dd, 1H, J=3.9, 15.3 Hz, $CH_2$), 2.05 (dd, 1H, J=3.9, 15.3 Hz, $CH_2$); $^{13}C$ NMR (500 MHz, $CDCl_3$): δ=155.5, 151.7, 150.1, 149.7, 129.9, 128.4, 128.3, 127.7, 127.5, 126.6, 126.2, 125.4, 125.0, 123.6, 123.5, 121.8, 121.7, 121.3, 113.3, 109.6, 81.6, 45.8. ESI MS m/z 408.1450 [M+Na$^+$]; calcd for $C_{23}H_{15}NNaO_5^+$: 408.0848.

Example 7

Synthesis of Dibenzylcyclooctyne Polyethylene glycol (i)

Figure 9:
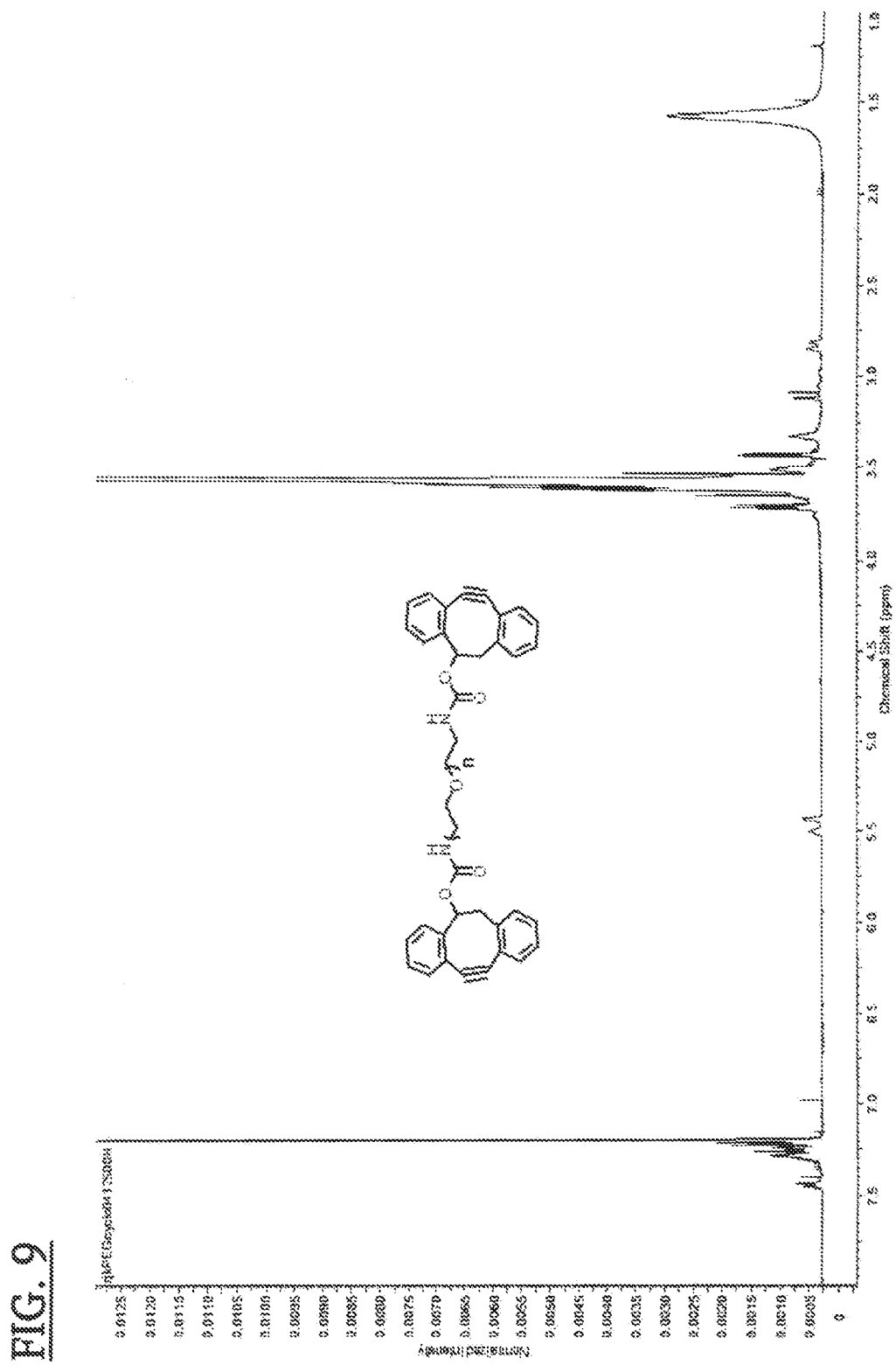
FIG. 9 is a $^1$HNMR spectra of DIBO-PEG made according to at least one embodiment of the present invention.

Polyethylene glycol bisamine (xi) (6.0 k, 100 mg, 0.017 mmol) was dissolved in 20 mL anhydrous $CH_2Cl_2$, then 6.8 uL triethanolamine (TEA) was added. Under argon carbonic acid, 5,6-(dihydro-11,12-didehydro-dibenzo[a,e]cycloocten-5-yl ester, 4-nitrophenyl ester (x) (prepared as set forth above in Example 6) (25 mg, 0.067 mmol) was added. After 24 hours the solvent was removed under vacuum and water was added to dissolve the product and dialysis against water with cut off MW 1000. The product was then lyophillized to afford Dibenzylcyclooctyne Polyethylene glycol (i) as white powder (80 mg, 80%). The $^1H$ NMR spectra for the reaction product (i) is attached as FIG. 9. The result of the $^1H$ NMR was as follows: $^1H$ NMR (500 MHz, $CDCl_3$): δ=7.51-7.23 (16H, aromatics), 5.51 (2H, dd, J=3.9, 15.3 Hz, CHOH), 3.70-3.60 (~550H, s, $OCH_2CH_2O$), 3.40 (4H, d, J=6.4 Hz, $CH_2NH$), 3.20 (dd, 2H, J=3.9, 15.3 Hz, $CH_2$), 2.91 (dd, 2H, J=3.9, 15.3 Hz, $CH_2$).

Example 8

Synthesis of Triarm PEG azide (ii)

Figure 10:
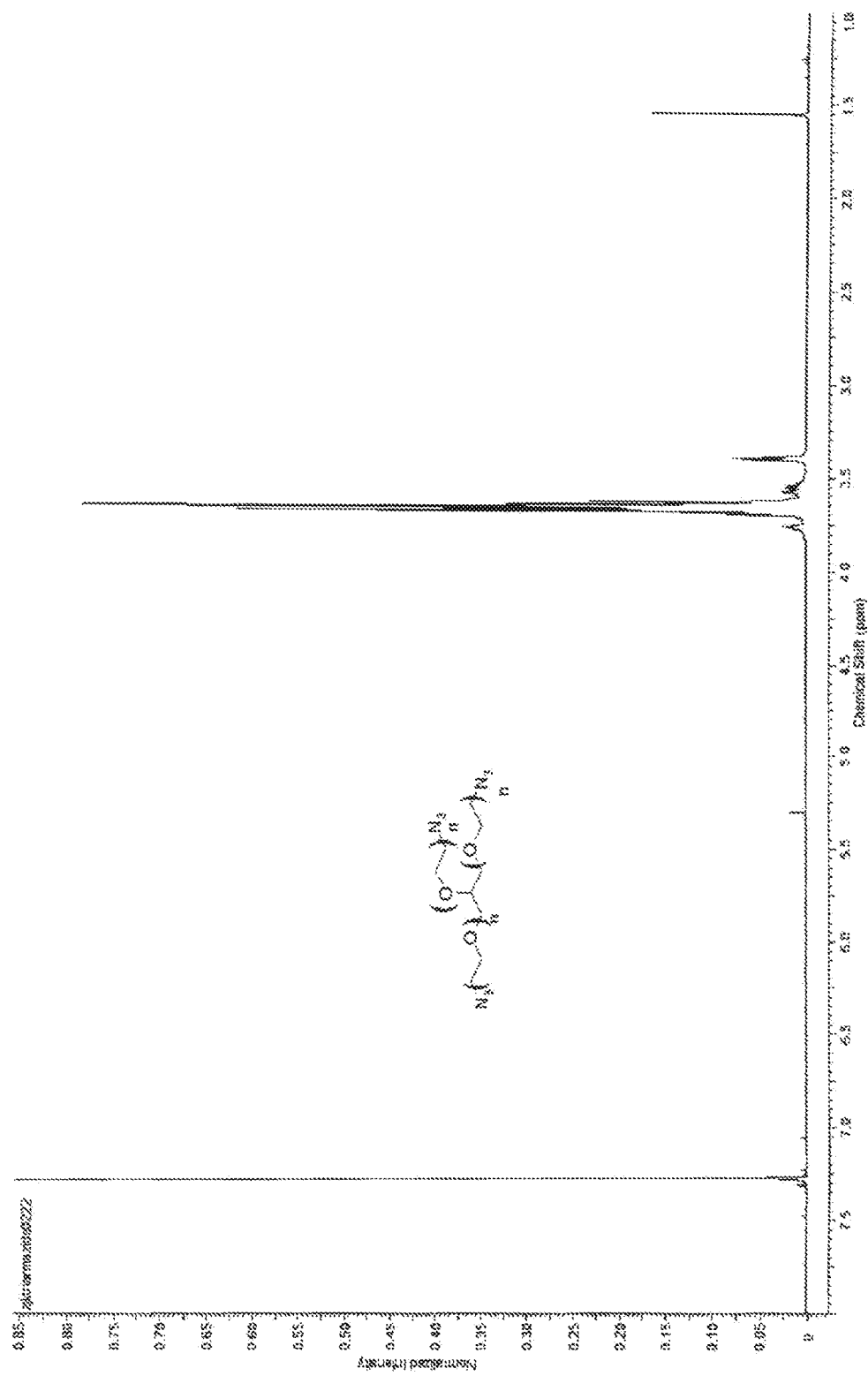
FIG. 10 is a $^1$H NMR spectra of glycerol ethoxylate triazide made according to at least one embodiment of the present invention.

Glycerol ethoxylate (4.67 g 4.67 mmol) was dissolved in 100 mL anhydrous $CH_2Cl_2$, then TEA (4.35 mL, 31.9 mmol) was added. Methanesulfonyl chloride (2.40 mL, 31.1 mmol) was then added dropwise via syringe to the solution under argon in an ice bath. After 1 hour the solution was removed from the ice bath and allowed to warm to room temperature for 24 hours. The salt was removed via filtration and the solution was concentrated under vacuum. Water (100 mL) was added to extract the desired compound. Sodium carbonate was added to the aqueous layer until the pH=8. Sodium azide (1.82 g, 28.0 mmol) was added and the reaction was heated at 85° C. for 24 hours. The solvent was removed under vacuum and extracted with 5×100 mL $CH_2Cl_2$ and dried over $Na_2SO_4$. The desired compound was eluted with $CH_2Cl_2$:methanol (15:1) on neutral Aluminum oxide to afford a Triarm PEG azide (ii) as colorless oil (2.1 g, 45%). The $^1H$ NMR spectra for the reaction product (ii) is attached as FIG. 10. The result of the $^1H$ NMR was as follows: $^1H$ NMR (500 MHz, $CDCl_3$): δ=3.70-3.63 (~84H, s, $OCH_2CH_2O$), 3.60-3.52 (5H, m, $CH_2CHCH_2$), 3.40 (t, 6H, J=5.0 Hz, $CH_2N3$).

Example 9

Figure 11:
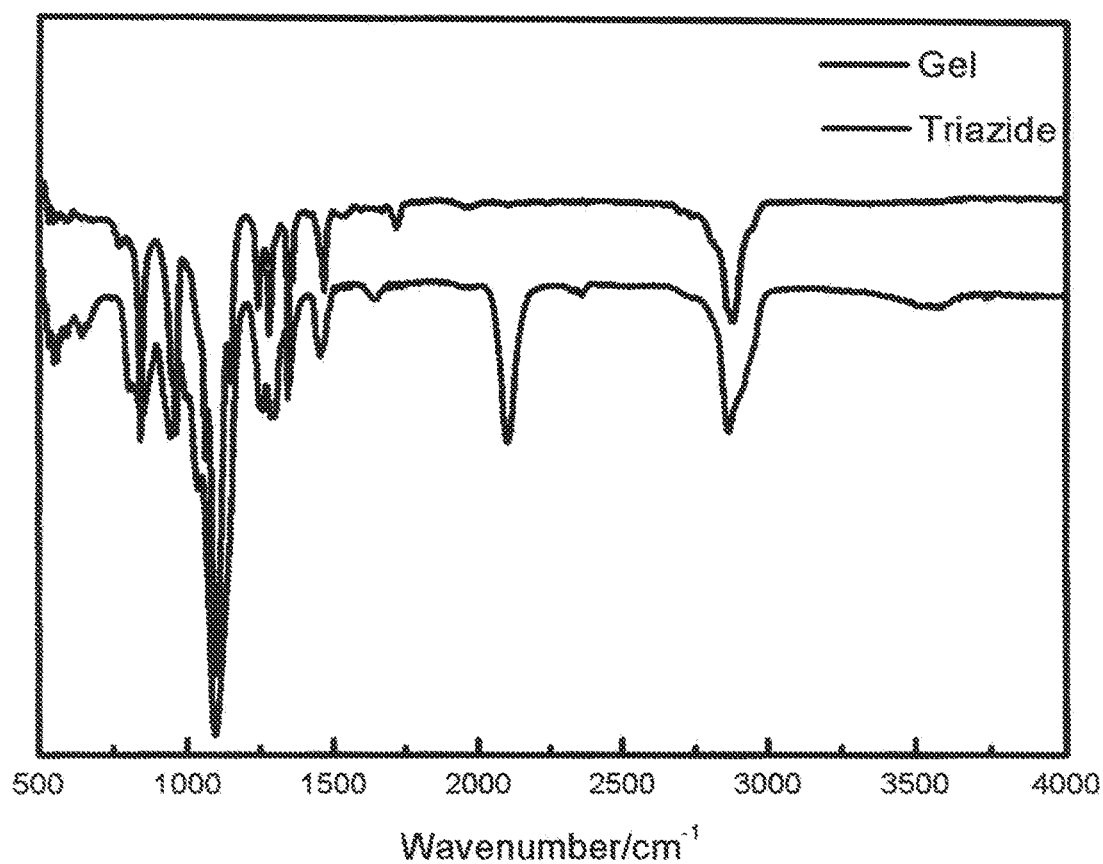
FIG. 11 is FTIR-ATR spectra of freeze dried hydrogels made according to at least one embodiment of the present invention verifying the loss of azide (2095 cm$^{-1}$).

Crosslinking of a Hydrogel Made According to at Least One Embodiment of the Current Invention To demonstrate the gelation of the two precursors in aqueous solution, a stoichiometric mixture of DIBO-functionalized PEG was dissolved in 50 uL ultrapure water, based on the calculation of 1:1 molar ratio for the DIBO group and azide group, 1.1 mg glycerol ethoxylate triazide is dissolved in 50 uL ultrapure water and these two solutions were mixed. Within 5 minutes, the solution gelled when agitated gently (FIG. 11). FTIR of the freeze-dried hydrogels confirms the disappearance of the azide groups. FIG. 11.

Example 10

Shear Rheology Analysis of a Hydrogel Made According to at Least One Embodiment of the Current Invention To assess whether the gel is suitable for injectable gel applications, an oscillatory shear rheology experiment was performed to study the gelation kinetics under applied mechanical forces. See, FIG. 3. Oscillatory shear measurements were made at 24° C. with a TA Instruments ARES-G2 rheometer equipped with 8 mm parallel plates and using a frequency of 10 rad/s (1.6 Hz) and a strain amplitude of 10%. Briefly, 100 µL of the 20 wt % DIBO-PEG solution was added to the plate followed by 100 µL of a 2.56 wt % glycerol ethoxylate triazide solution. The oscillatory shear measurement was conducted immediately.

To maintain hydration of the hydrogel sample during the experiment, the lower plate fixture included a solvent trap filled with an aqueous solution of DIBO-PEG and glycerol ethoxylate triazide (1:1). The large scatter in the data at times less than 600 s is a consequence of the very low viscosity of the solution before sufficient crosslinking was achieved. As a consequence, the torque values are too low to obtain reliable readings from the force transducer. See FIG. 3. However, after 600 s the torque magnitude was sufficiently high, and both G' (the elastic part of the complex modulus, G*) and G" (the viscous component of G*) increased exponentially with time.

At the beginning of the experiment, the solution is a viscous liquid and it is expected that G">G'. The crossover of G' and G" near t~1000 represents the gel point, where the crosslinking reaction has proceeded sufficiently in that the material transforms from a viscous liquid to a viscoelastic solid. After about 2.5 h, the dynamic moduli reached equilibrium values, indicating that the crosslinking reaction was complete. The gel was fully hydrated throughout the experiment and at the end of the reaction the gel contained 96.1% water and the plateau modulus, GN' was ~0.8 kPa. This corresponds to a crosslink density of 8.6 mol/m$^3$, which was calculated using the classical theory of rubber elasticity. The loss factor tan δ (G"/G') decreased from a value of ~1, which is typical of a viscous liquid to a value of ~0.25 at the end of the reaction, which is consistent with the formation of a viscoelastic solid (tan δ is zero for an elastic solid). This reaction was also shown to be strain sensitive.

Example 11

Biocompatibility Assay with Human Mesenchymal Stem Cells

Human mesenchymal stem cells (hMSCs) were used to test the influence of the hydrogel crosslinking on cell viability. hMSCs (passage 5, 500,000 cells, Lonza, Basel, Switzerland) were suspended in 25 µL of 20 wt % DIBO-PEG in α-MEM basal Media (Lonza). 25 µL of 2.56 wt % glycerol ethoxylate triazide in α-MEM basal Media was added to the cell suspension. The samples were mixed via gentle pipetting and placed in a mold to solidify. After 5 min, the hydrogels were transferred by spatula to a 12-well plate and cultured in α-MEM basal Media for 24 h in a 37° C., 5% CO$_2$ incubator. A live dead assay (Invitrogen, Carlsbad, Calif.) was performed. 1.5 µL of 1 mg/mL Calcein AM and 0.1 µL of 2 mM ethidium homodimer-1 was added per mL of culture media and the samples were incubated for 10 minutes. The samples were then washed with media and viewed on a 1×81× microscope (Olympus, Center Valley, Pa.). The encapsulation of cells and presence of media additives did not affect the gelation process. The dominant green fluorescence from live cells in the live/dead cell staining after 24 h of culture demonstrates the excellent biocompatibility of these hydrogels (>95%). Tri-arm molecules not converted to the azide do not gel as expected and hMSCs mixed with the individual components do not exhibit toxicity (data not shown) under identical concentration conditions.

What is claimed is:

1. A covalently crosslinked hydrogel comprising the strain-induced reaction product of an 8-member cycloalkyne functionalized polyalkylene glycol and a water soluble three-arm glycerol ethoxylate triazide.

2. The covalently crosslinked hydrogel of claim 1 wherein said 8-member cycloalkyne functionalized polyalkylene glycol is a polymer selected from the group consisting of 8-member cycloalkyne functionalized polyethylene glycol, 8-member cycloalkyne functionalized polypropylene glycol and combinations thereof.

3. The covalently crosslinked hydrogel of claim 1 wherein said 8-member cycloalkyne functionalized polyalkylene glycol has a molecular mass from about 500 Da to about 12000 Da.

4. The covalently crosslinked hydrogel of claim 1 wherein said 8-member cycloalkyne functionalized polyalkylene glycol is dibenzylcyclooctyne functionalized polyethylene glycol.

5. The covalently crosslinked hydrogel of claim 4 wherein said 8-member cycloalkyne functionalized polyalkylene glycol is in an aqueous solution comprising from about 1% to about 40% weight percent dibenzylcyclooctyne functionalized polyethylene glycol.

6. The covalently crosslinked hydrogel of claim 4 wherein said covalently crosslinked hydrogel is formed by the strain-induced cycloaddition of said dibenzylcyclooctyne functionalized polyethylene glycol and said water soluble three-arm glycerol ethoxylate triazide.

7. The covalently crosslinked hydrogel of claim 4 wherein said is dibenzylcyclooctyne functionalized polyethylene glycol has a mass average molecular weight of from about 1,000 to about 20,000.

8. The covalently crosslinked hydrogel of claim 4 wherein said dibenzylcyclooctyne functionalized polyethylene glycol has the following formula:

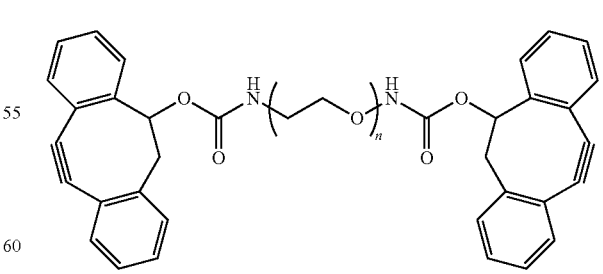

wherein n is an integer from about 6 to about 300.

9. The covalently crosslinked hydrogel of claim 8 wherein n is 6 or 7.

10. The covalently crosslinked hydrogel of claim 1 wherein said water soluble three-arm glycerol ethoxylate triazide is in an aqueous solution comprising from about 1% to about 40% weight percent of said water soluble three-arm glycerol ethoxylate triazide.

11. The covalently crosslinked hydrogel of claim 1 wherein said covalently crosslinked hydrogel is formed by the strain-induced cycloaddition of a dibenzylcyclooctyne functionalized polyethylene glycol and a water soluble three-arm glycerol ethoxylate triazide.

12. The covalently crosslinked hydrogel of claim 1 having a crosslink density of from about 2 to about 300 mol/m$^3$.

13. The covalently crosslinked hydrogel of claim 1 having a loss factor (tan δ) of from about 0.10 to about 0.50.

14. The covalently crosslinked hydrogel of claim 1 further comprising an additive selected from the group consisting of cells, collagen, deceullarized tissue, gelatin and combinations thereof.

15. The covalently crosslinked hydrogel of claim 14 wherein said additive is encapsulated within said covalently crosslinked hydrogel.

16. The covalently crosslinked hydrogel of claim 1 wherein said covalently crosslinked hydrogel comprises from about 40% to about 99.9% water.

17. The covalently crosslinked hydrogel of claim 1 wherein said water soluble three-arm glycerol ethoxylate triazide has the formula:

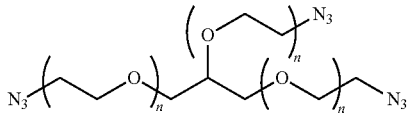

wherein each n is an integer from about 8 to about 30.

18. The covalently crosslinked hydrogel of claim 1 which has the formula:

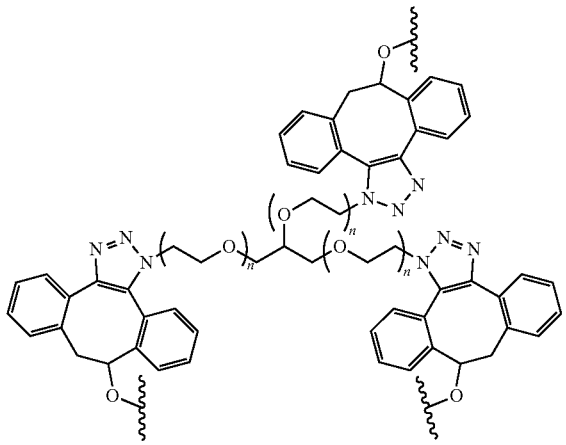

wherein n is an integer from about 8 to about 30.

19. A method of making the covalently crosslinked hydrogel of claim 1, comprising:
A) preparing an aqueous solution containing a 8-member cycloalkyne functionalized polyalkylene glycol;
B) preparing an aqueous solution containing a water soluble three-arm glycerol ethoxylate triazide;
C) combining the solution of step A with the solution of step B; and
D) applying a strain to the mixture of step C until covalent crosslinks form between said 8-member cycloalkyne functionalized polyalkylene glycol and said water soluble three-arm glycerol ethoxylate triazide.

20. The method of claim 19, wherein said 8-member cycloalkyne functionalized polyalkylene glycol is a polymer selected from the group consisting of 8-member cycloalkyne functionalized polyethylene glycols, 8-member cycloalkyne functionalized polypropylene glycols and combinations thereof.

21. The method of claim 19, wherein said 8-member cycloalkyne functionalized polyalkylene glycol is dibenzylcyclooctyne functionalized polyethylene glycol.

22. The method of claim 19, wherein the aqueous solution of Step A contains from about 1% to about 40% weight percent of said 8-member cycloalkyne functionalized polyalkylene glycol.

23. The method of claim 19, wherein the aqueous solution of Step B contains from about 1% to about 40% weight percent of said water soluble three-arm glycerol ethoxylate triazide.

24. The method of claim 21, wherein said dibenzylcyclooctyne functionalized polyethylene glycol has a mass average molecular weight of from about 1,000 to about 20,000.

25. The method of claim 19, further comprising the step of introducing the mixture of step C into a living organism, prior to step D.

26. The method of claim 25, wherein step D occurs in vivo.

27. The method of claim 19, wherein the mixture of step C has a loss factor (tan δ) greater than or equal to about 1.0.

28. The method of claim 19, further comprising the step of adding an additive selected from the group consisting of cells, collagen, decellularized tissue, gelatin and combinations thereof into the aqueous solution of step A and/or the aqueous solution of step B.

29. The method of claim 28, wherein said additive is encapsulated within said covalently crosslinked hydrogel.

30. The method of claim 19, wherein the strain applied in step D is an oscillatory shear strain of from 5% to 15%.

* * * * *